(12) United States Patent
Taylor

(10) Patent No.: US 8,932,613 B2
(45) Date of Patent: Jan. 13, 2015

(54) ECTOPARASITE CONTROL METHOD

(75) Inventor: Wendy Sue Taylor, Landenberg, PA (US)

(73) Assignee: E I du Pont de Nemours and Company, Wilmington, DE (US)

(*) Notice: Subject to any disclaimer, the term of this patent is extended or adjusted under 35 U.S.C. 154(b) by 595 days.

(21) Appl. No.: 12/670,494

(22) PCT Filed: Jul. 28, 2008

(86) PCT No.: PCT/US2008/071287
§ 371 (c)(1),
(2), (4) Date: Jan. 25, 2010

(87) PCT Pub. No.: WO2009/018185
PCT Pub. Date: Feb. 5, 2009

(65) Prior Publication Data
US 2010/0204281 A1    Aug. 12, 2010

Related U.S. Application Data

(60) Provisional application No. 60/962,568, filed on Jul. 30, 2007.

(51) Int. Cl.
A01N 25/02      (2006.01)
A61K 31/4155    (2006.01)
A01N 43/56      (2006.01)

(52) U.S. Cl.
CPC .......... *A01N 43/56* (2013.01); *A61K 31/4155* (2013.01)
USPC .......................................... 424/405; 514/183

(58) Field of Classification Search
USPC .................................................. 424/405
See application file for complete search history.

(56) References Cited

U.S. PATENT DOCUMENTS

| | | | |
|---|---|---|---|
| 6,001,384 A | 12/1999 | Jeannin | |
| 2004/0198984 A1 | 10/2004 | Lahm et al. | |
| 2007/0161037 A1 | 7/2007 | Gutteridge | |
| 2009/0036407 A1 | 2/2009 | Taylor | |
| 2009/0036497 A1 | 2/2009 | Taylor | |
| 2009/0036498 A1 | 2/2009 | Taylor | |
| 2009/0036499 A1 | 2/2009 | Taylor | |
| 2009/0104145 A1 | 4/2009 | Hughes et al. | |
| 2009/0275471 A1* | 11/2009 | Funke et al. | 504/100 |
| 2010/0056469 A1* | 3/2010 | Langewald et al. | 514/53 |
| 2010/0120616 A1* | 5/2010 | Breuninger et al. | 504/100 |
| 2010/0197738 A1 | 8/2010 | Taylor | |
| 2010/0210601 A1* | 8/2010 | Taylor | 514/143 |
| 2011/0015153 A1 | 1/2011 | Taylor | |

FOREIGN PATENT DOCUMENTS

| | | |
|---|---|---|
| EP | 1717237 A1 | 2/2005 |
| GB | 2321012 A1 | 7/1998 |
| WO | 98/07423 A1 | 2/1998 |
| WO | 0170671 A2 | 9/2001 |
| WO | 03015518 A1 | 2/2003 |
| WO | 03015519 A1 | 2/2003 |

(Continued)

OTHER PUBLICATIONS

Londershaunsen Michael: "Approaches to new parasiticides" Pesticide Science, vol. 48, No. 4, 1996, p. 269-292, XP002561859 ISSN: 0031-613X.
S.K. Meegalla et al. Bioorg. & Med. Chem. Lett. (2006), 1702-1706.
P.N.R. Usherwood et al., "Towards the development of ryanoid insecticides with low mammalian toxicity" retreived from STN International Database accession No. 9725325 & Toxicology Letters, vol. 82/83 No. COM 1995 pp. 247-254.
G.P. Lahm et al: "Insecticidal antrhanilic diamides:A new class of potent ryanodine receptor activators" Bioorganic & Medical Chemistry Letters, vol. 15, Sep. 13, 2005 pp. 4898-4906.
PCT/US2008/071288 International Search Report, Mar. 4, 2010.
PCT/US/2008/071288 International Preliminary Report on Patentability, Mar. 9, 2010.

(Continued)

*Primary Examiner* — Audrea Buckley

(57) ABSTRACT

This invention relates to a method of controlling or preventing infestations of ectoparasites, preferably hematophageous ectoparasites, on an animal by administering to the animal a composition comprising an parasiticidally effective amount of a compound of Formula 1, or an N-oxide, or a pharmaceutically or veterinarily acceptable salt thereof,

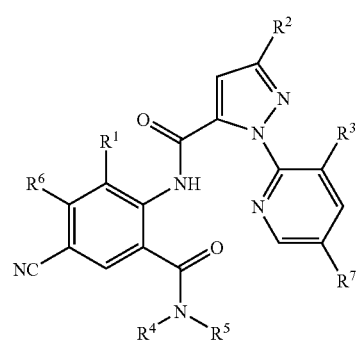

wherein
$R^1$ is Me, Cl, Br or F;
$R^2$ is F, Cl, Br, $C_1$-$C_4$ haloalkyl or $C_1$-$C_4$ haloalkoxy;
$R^3$ is F, Cl or Br;
$R^4$ is H; $C_1$-$C_4$ alkyl, $C_3$-$C_4$ alkenyl, $C_3$-$C_4$ alkynyl, $C_3$-$C_5$ cycloalkyl, or $C_4$-$C_6$ cycloalkylalkyl, each optionally substituted with one substituent selected from the group consisting of halogen, CN, SMe, S(O)Me, $S(O)_2$Me, and OMe;
$R^5$ is H or Me;
$R^6$ is H, F or Cl; and
$R^7$ is H, F or Cl.

5 Claims, No Drawings

(56) References Cited

FOREIGN PATENT DOCUMENTS

| WO | 2004/067528 A1 | 8/2004 |
| WO | 2004067528 A1 | 8/2004 |
| WO | 2006007595 A2 | 1/2006 |
| WO | 2006/068669 A1 | 6/2006 |
| WO | WO 2006/108552 * | 10/2006 |
| WO | 2006128867 A1 | 12/2006 |
| WO | 2007017433 A2 | 2/2007 |
| WO | 2007020877 A1 | 2/2007 |
| WO | WO2007/020877 A1 | 2/2007 |
| WO | 2008104503 A1 | 9/2008 |
| WO | 2008125410 A2 | 10/2008 |

OTHER PUBLICATIONS

PCT/US2008/071287 International Search Report (International Phase of this Application), Feb. 11, 2010.

PCT/US2008/071287 International Preliminary Report on Patentability (International Phase of this Application), Feb. 2, 2010.

Ohkawa et al., Pesticide Chemistry, Wiley Verlag Chapters 11 and 12 Jul. 17, 2007.

Office Actions and Responses in U.S. Appl. No. 12/182,566, Jul. 2, 2012.

Office Actions and Responses in U.S. Appl. No. 12/670,663, Jun. 14, 2012.

Office Actions and Responses in U.S. Appl. No. 12/182,551, Feb. 1, 2012.

* cited by examiner

ECTOPARASITE CONTROL METHOD

FIELD OF THE INVENTION

This invention relates to certain methods for controlling ectoparasitic insects on homeothermic animals

BACKGROUND OF THE INVENTION

Ectoparasitic insects are particularly bothersome for animals including humans. They are annoying as well as possibly harmful due to the potential transmission of diseases. Although substantial need has existed in the industry for products which control or eradicate such ectoparasites, prior art attempts have failed to provide effective formulations which are capable of fully eradicating or controlling them while also being non-toxic to humans and animals.

In an attempt to meet the consumer demand for products of this nature, various pesticides, insecticides and insect repellant formulations have been developed. These products often suffer from drawbacks relating to their toxicity or lack of efficacy due to evolved resistance of the parasites. There is a pressing need therefore for new chemical compounds efficacious against such pests which are relatively non-toxic to the animal species they are used to protect.

SUMMARY OF THE INVENTION

This invention relates to a method of controlling or preventing infestations of an ectoparasitic insect, preferably a hematophageous ectoparasitic insect, on an animal by administering to the animal a composition comprising an parasiticidally effective amount of a compound of Formula 1, or an N-oxide, or a salt thereof,

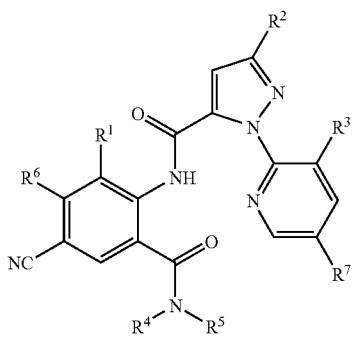

wherein $R^1$ is Me, Cl, Br or F;

$R^2$ is F, Cl, Br, $C_1$-$C_4$ haloalkyl or $C_1$-$C_4$ haloalkoxy;

$R^3$ is F, Cl or Br;

$R^4$ is H; $C_1$-$C_4$ alkyl, $C_3$-$C_4$ alkenyl, $C_3$-$C_4$ alkynyl, $C_3$-$C_5$ cycloalkyl, or $C_4$-$C_6$ cycloalkylalkyl, each optionally substituted with one substituent selected from the group consisting of halogen, CN, SMe, S(O)Me, S(O)$_2$Me, and OMe;

$R^5$ is H or Me;

$R^6$ is H, F or Cl; and $R^7$ is H, F or Cl.

The invention also comprises a compound of Formula 1 for use as a medicament.

The invention also relates to the use of a compound of Formula 1 in the manufacture of a medicament for the treatment of an infestation of an ectoparasitic insect on a animal

DETAILS OF THE INVENTION

As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but may include other elements not expressly listed or inherent to such composition, mixture, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

In the above recitations, the term "alkyl", used either alone or in compound words such as "alkylthio" or "haloalkyl" includes straight-chain or branched alkyl, such as, methyl, ethyl, n-propyl, i-propyl, or the different butyl isomers. The term "halogen", either alone or in compound words such as "haloalkoxy", includes fluorine, chlorine, bromine or iodine. Further, when used in compound words such as "haloalkyl", or "haloalkoxy", said alkyl or alkoxy may be partially or fully substituted with halogen atoms which may be the same or different. Examples of "haloalkyl" include $F_3C$, $ClCH_2$, $CF_3CH_2$ and $CF_3CCl_2$. Examples of "haloalkoxy" include $CF_3O$, $HCF_2O$, $CCl_3CH_2O$, $HCF_2CH_2CH_2O$ and $CF_3CH_2O$.

One skilled in the art will appreciate that not all nitrogen-containing heterocycles can form N-oxides since the nitrogen requires an available lone pair for oxidation to the oxide; one skilled in the art will recognize those nitrogen-containing heterocycles which can form N-oxides. One skilled in the art will also recognize that tertiary amines can form N-oxides. Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocyclic Chemistry*, vol. 22, pp 390-392, A. R. Katritzky and A. J. Boulton, Eds., Academic Press.

Compounds of this invention can exist as one or more stereoisomers. The various stereoisomers include enantiomers, diastereomers, atropisomers and geometric isomers. One skilled in the art will appreciate that one stereoisomer may be more active and/or may exhibit beneficial effects when enriched relative to the other stereoisomer(s) or when separated from the other stereoisomer(s). Additionally, the skilled artisan knows how to separate, enrich, and/or to selectively prepare said stereoisomers. Accordingly, the present invention comprises compounds selected from Formula 1, N-oxides and salts thereof. Pharmaceutically or veterinarily acceptable salts, suitable to the mode of administration, are contemplated. The compounds of the invention may be present as a mixture of stereoisomers, individual stereoisomers, or as an optically active form.

The salts of the compounds of the invention include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. In the compositions and methods of this invention, the salts of the compounds of the invention are preferably acceptable for the veterinary/pharmaceutical uses described herein.

Of note are compounds of Formula 1 wherein
  $R^4$ is H or $C_1$-$C_4$ alkyl optionally substituted with one substituent selected from the group consisting of CN, SMe and OMe;
  $R^5$ is H or Me;
  $R^6$ is H; and
  $R^7$ is H.
Of further note are:
a) Compounds of Formula 1 wherein
  $R^1$ is Me or Cl;
  $R^2$ is Cl, Br, $CF_3$, $OCF_2H$, $OCF_3$ or $OCH_2CF_3$; and
  $R^4$ is H, Me, Et, i-Pr, t-Bu, $CH_2CN$, $CH(Me)CH_2SMe$ or $C(Me)_2CH_2SMe$.
b) Compounds of a) above wherein
  $R^2$ is Cl, Br, $CF_3$ or $OCH_2CF_3$;
  $R^4$ is H, Me, Et or i-Pr; and
  $R^5$ is H.
c) Compounds of b) wherein:
  $R^1$ is Me; $R^2$ is Br; $R^3$ is Cl; $R^4$ is Me.
Of further note are compounds of a, b, c above wherein $R^6$ is H; and $R^7$ is H.
A compound of special interest is:

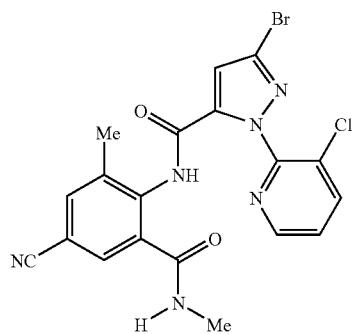

or 3-bromo-1-(3-chloro-2-pyridinyl)-N-[4-cyano-2-methyl-6-[(methylamino)carbonyl]-phenyl]-1H-pyrazole-5-carboxamide.

The preferred compositions of the present invention are those, which comprise the above preferred compounds. The preferred methods of use are those involving the above-preferred compounds.

"Ectoparasitic insect" means insect ectoparasites of warm blooded animals

Hematophagous insect ectoparasites are ectoparasitic insects which attack their hosts by ingesting blood. By "ingesting" is meant not only piercing the animal integument and sucking the blood from the circulatory system, but also consuming tissue or tissue fluids of the host and thereby inevitably consume blood or blood constituents. Included within the definition of hematophageous ectoparasitic insects are fleas, ticks, biting flies, mites, lice, and true bugs.

"Homeothermic Animals" means warm blooded animals. The term is meant to include all such animals including humans and particularly important agronomic or companion animals such cattle, sheep, horses, goats, pigs, llamas, camels, water buffalo, donkeys, rabbits, fallow deer, reindeer, minks, chinchillas, ferrets, raccoons, chickens, geese, turkeys, ducks, dogs, cats, mice rats, or the like.

For the purposes of the present invention, the term flea is understood to refer to all the usual or accidental species of parasitic flea of the order Siphonaptera. One of the Siphonaptera families known to infest companion animals is Pulicidae such as Archaeopsyllinae (cat and dog fleas), Spilopsyllinae (rabbit fleas), or the like.

Of particular interest are the species *Ctenocephalides*, in particular *C. felis* and *C. canis*, rat fleas (*Xenopsylla cheopis*) and human fleas (*Pulex irritans*).

For the purposes of this invention the terms ticks and mites are meant to refer the blood-feeding arthropod parasites that belong to the order Acarina. From the Order Acarina, some of the ticks and mites known to infest production and companion animals are, *Argas* spp., *Ornithodoros* spp., *Dermanyssus gallinae*, *Boophilus* spp., *Rhipicephalus* spp., *Amblyomma* spp., *Dermacentor* spp., *Hyalomma* spp., *Ixodes* spp., *Psoroptes* spp., *Chorioptes* spp., *Sarcoptes* spp., *Cheyletiella* spp., and the like.

There are two well-established families of ticks, the Ixodidae (hard ticks), and Argasidae (soft ticks). Ticks often produce injury after infestation of animals in three respects: direct damage caused by parasitism such as local injury and blood loss; by toxins injected by the parasites and by the transmission of diseases. Especially in companion animals, ticks may be the source of zoonotic diseases.

For the purpose of this invention "lice" (singular: louse), are ectoparasites of the order Phthiraptera. Among the Phthiraptera families known to be parasites of animals are: Trichodectidae such as *Bovicola bovis* (important cattle-biting louse), *B. ovis* (sheep-biting louse) or *B. equi* (horsebiting louse); Haematopimidae such as *Haematopinus suis* (hog louse), or *H. asini* (horse sucking louse); Linognathidae such as *Linognathus stenopsis* (goat sucking louse) or *L. vituli* (long-nosed cattle louse); or the like.

"Flies" are insects in the order Diptera, meaning "two-winged". True flies have one pair of wings used for flying. Posterior to the wings is a pair of stalked knob-like structures (called halteres), which are organs of balance. Flies undergo complete metamorphosis, i.e. the life cycle consists of the following stages: egg, larva (called a maggot), pupa, and adult. Each stage of the life cycle may be a target for control and intervention.

Flies may be categorized into two functional categories "biting" and "non-biting" of which biting flies are the primary focus here.

"Biting flies" have specially adapted mouthparts well suited for piercing the host animal integument. The stable fly *Stomoxys calcitrans* is a good example of a biting fly. The stable fly has a proboscis which is used to pierce the skin and imbibe blood. Both the males and the females are bloodfeeders. The stable fly is often the only biting, blood-sucking fly breeding in any appreciable numbers in and around confined-animal production facilities, Another example of a biting fly is the horn fly, *Haematobia irritans irritans*, which like the stable fly is a bloodsucker and has great economic impact. Like the stable fly the horn fly has piercing/sucking mouthparts.

A "parasiticidally effective amount" is the amount of active ingredient needed to achieve an observable effect diminishing the occurrence or activity of the target parasite pest. One skilled in the art will appreciate that the parasitically effective dose can vary for the various compounds and compositions of the present invention, the desired parasitical effect and duration, the target invertebrate pest species, the animal to be protected, the mode of application and the like, and the amount needed to achieve a particular result can be determined through simple experimentation "Treating" or "Treatment" as it applies to infestation refers to both the prevention and control of the infestation.

"Parenteral" as a mode of application means taken into the body or administered in a manner other than through the digestive tract, as by injection.

"Enteral" as a mode of application means take into the body or administered through the digestive tract as by oral administration.

Embodiments of the present invention include:

Embodiment 1

The method or use described in the Summary of the Invention wherein the ectoparasitic insect is a hematophageous ectoparasitic insect Embodiment 2

The method or use of as described in the Summary of the Invention wherein
$R^1$ is Me or Cl;
$R^2$ is Cl, Br, $CF_3$, $OCF_2H$, $OCF_3$ or $OCH_2CF_3$; and
$R^4$ is H, Me, Et, i-Pr, t-Bu, $CH_2CN$, $CH(Me)CH_2SMe$ or $C(Me)_2CH_2SMe$.

Embodiment 3

The method or use of as described in the Summary of the Invention wherein
$R^2$ is Cl, Br, $CF_3$ or $OCH_2CF_3$;
$R^4$ is H, Me, Et or i-Pr; and
$R^5$ is H.

Embodiment 4

The method or use of as described in the Summary of the Invention wherein the Compound is
3-bromo-1-(3-chloro-2-pyridinyl)-N-[4-cyano-2-methyl-6-[(methylamino)carbonyl]phenyl]-1H-pyrazole-5-carboxamide Embodiment 5

The method or use of as described in the Summary of the Invention or in any of the previous embodiments wherein the ectoparasite is a hematophageous ectoparasite Embodiment 6

The method or use of Embodiment 5 wherein the hematophageous ectoparasite is selected from the group consisting of fleas, ticks, lice, mites, and biting flies.

Embodiment 7

The method or use of any of the previous embodiments wherein the administering is oral.

Embodiment 8

The method or of any of the previous embodiments wherein the administering is parenteral.

Embodiment 9

The method or use of any of the previous embodiments wherein the administering is topical.

Embodiment 10

The method or use of any of the previous embodiments wherein the animal is a homeothermic animal.

Embodiment 10a

The method or use of Embodiment 10 wherein the animal is a cat or dog.

Embodiment 11

The method or use of embodiment 10 wherein the animal is a herd animal.

Embodiment 12

The method or use of any of the previous embodiments wherein the composition comprises at least one additional component selected from the group consisting of solvents and/or carriers, emulsifiers and/or dispersing agents.

Embodiment 13

The method or use of Embodiment 12 wherein the composition comprises at least one additional biologically active compound or agent.

Embodiment 14

The method or use of Embodiment 13 wherein the additional biologically active compound or agent is selected from the group consisting of macrocyclic lactones, acetyl cholinesterase inhibitors, arthropod growth regulators, GABA-gated chloride channel antagonists, mitochondrial electron transport inhibitors, nicotinic acetylcholine agonists/antagonists/activator, oxidative phosphorylation inhibitors, anthelminthics, sodium channel modulators or other antiparasitic compounds.

Embodiment 15

The method or use of Embodiment 14 wherein said biologically active compound is a macrocyclic lactone.

Embodiment 16

The method or use of Embodiment 14 wherein said biologically active compound is an acetyl cholinesterase inhibitor selected from the group of organophosphates and carbamates.

Embodiment 17

The method or use of Embodiment 14 wherein said biologically active compound is an arthropod growth regulator selected from the group of chitin synthesis inhibitors, ecdysone agonists/disruptors, lipid biosynthesis inhibitor and juvenile hormone mimics.

Embodiment 18

The method or use of Embodiment 14 wherein said biologically active compound is a GABA-gated chloride channel antagonist.

Embodiment 19

The method or use of Embodiment 14 wherein said biologically active compound is a mitochondrial electron transport inhibitor.

Embodiment 20

The method or use of Embodiment 14 wherein said biologically active compound is a nicotinic acetylcholine agonist/antagonist/activator.

Embodiment 21

The method or use of Embodiment 14 wherein said biologically active compound is an oxidative phosphorylation inhibitor.

Embodiment 22

The method or use of Embodiment 14 wherein said biologically active compound is an anthelminthic.

Embodiment 23

The method or use of Embodiment 14 wherein said biologically active compound is a sodium channel modulator.

This invention relates to a method of controlling or prevention infestations of an ectoparasite, preferably a hematophageous ectoparasite, on an animal by administering to the animal a composition comprising an parasiticidally effective amount of a compound of Formula 1, or an N-oxide, or a pharmaceutically or veterinarily acceptable salt thereof, The compounds of Formula 1 can be used for the protection of an animal from an ectoparasitic insect by oral, topical or parenteral administration of the compound.

Therefore, the invention is understood to include the compounds of Formula 1 (and compositions containing them) for use as an animal medicament, or more particularly a ectoparasiticidal animal medicament. The animals to be protected include those delineated in any of Embodiments 10, 10a, or 11. The ectoparasitic insect pests include those delineated in Embodiments 5 or 6. The medicament may be in oral, topical or parenteral dosage forms.

The invention is also understood to include the use of compounds of Formula 1 or any of Embodiments 2, 3, or 4 in the manufacture of medicaments for the protection of an animal from a an invertebrate parasitic pest. The animals to be protected include those delineated in any of Embodiments 10, 10a, or 11. The ectoparasitic insect pests include those delineated in Embodiments 5 or 6. The medicament may be in oral, topical or parenteral dosage forms.

The invention is also understood to include compounds of Formula 1 or any of Embodiments 2, 3, or 4 for use in the manufacture of medicaments for the protection of an animal from an invertebrate parasitic pest. The animals to be protected include those delineated in any of Embodiments 10, 10a, or 11. The ectoparasitic insect pests include those delineated in Embodiments 5 or 6. The medicament may be in oral, topical or parenteral dosage forms.

The invention is also understood to include compounds of Formula 1 or any of Embodiments 2, 3, or 4 packaged and presented for the protection of an animal from an invertebrate parasitic pest. The animals to be protected include those delineated in any of Embodiments 10, 10a, or 11. The ectoparasitic insect pests include those delineated in Embodiments 5 or 6. The compounds of the invention may be packaged and presented as oral, topical or parenteral dosage forms.

The invention is also understood to include a process for manufacturing a composition for protecting an animal from an invertebrate parasitic pest characterized in that a compound of Formula 1 is admixed with at least one pharmaceutically or veterinarily acceptable carrier. The animals to be protected include those delineated in any of Embodiments 10, 10a, or 11. The ectoparasitic insect pests include those delineated in Embodiments 5 or 6. The compositions of the invention may be packaged and presented as oral, topical or parenteral dosage forms.

The compounds of Formula 1 which can be used according to the invention, have an excellent action on ectoparasitic insects, particularly hematophageous ectoparasitic insects. The compounds are uniquely adapted to enter and spread through the circulatory of the host whilst being very well tolerated by the animal. The invention thus represents a genuine enrichment of the art.

The compounds according to the invention possess a good ectoparasiticidal activity, whilst being of low toxicity to animals. The compounds of Formula 1 can be prepared by the methods as described in US Patent Publication 2006/0111403A1 (herein incorporated by reference to the extent not inconsistent with the disclosure herein) and variations readily apparent to the skilled artisan.

Synthetic methods for the preparation of N-oxides of heterocycles and tertiary amines are very well known by one skilled in the art including the oxidation of heterocycles and tertiary amines with peroxy acids such as peracetic and m-chloroperbenzoic acid (MCPBA), hydrogen peroxide, alkyl hydroperoxides such as t-butyl hydroperoxide, sodium perborate, and dioxiranes such as dimethydroxirane. These methods for the preparation of N-oxides have been extensively described and reviewed in the literature, see for example: T. L. Gilchrist in *Comprehensive Organic Synthesis*, vol. 7, pp 748-750, S. V. Ley, Ed., Pergamon Press; M. Tisler and B. Stanovnik in *Comprehensive Heterocyclic Chemistry*, vol. 3, pp 18-20, A. J. Boulton and A. McKillop, Eds., Pergamon Press; M. R. Grimmett and B. R. T. Keene in *Advances in Heterocyclic Chemistry*, vol. 43, pp 149-161, A. R. Katritzky, Ed., Academic Press; M. Tisler and B. Stanovnik in *Advances in Heterocyclic Chemistry*, vol. 9, pp 285-291, A. R. Katritzky and A. J. Boulton, Eds., Academic Press; and G. W. H. Cheeseman and E. S. G. Werstiuk in *Advances in Heterocy-*

*clic Chemistry*, vol. 22, pp 390-392, A. R. Katritzky and A. J. Boulton, Eds., Academic Press.

The following compounds, by way of example and not by limitation, are expected to be advantageous in the practice of the invention.

TABLE 1

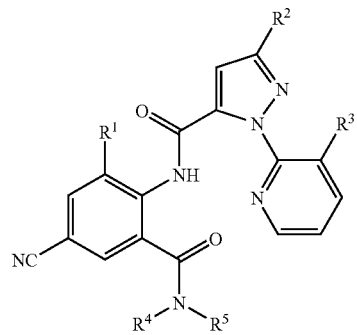

| R¹ | R² | R³ | R⁴ | R⁵ |
|---|---|---|---|---|
| Me | Cl | F | H | H |
| Me | Cl | F | Me | H |
| Me | Cl | F | Et | H |
| Me | Cl | F | i-Pr | H |
| Me | Cl | F | t-Bu | H |
| Me | Cl | F | CH₂CN | H |
| Me | Cl | F | CH(Me)CH₂SMe | H |
| Me | Cl | F | C(Me)₂CH₂SMe | H |
| Me | Cl | F | Me | Me |
| Me | Cl | Cl | H | H |
| Me | Cl | Cl | Me | H |
| Me | Cl | Cl | Et | H |
| Me | Cl | Cl | i-Pr | H |
| Me | Cl | Cl | t-Bu | H |
| Me | Cl | Cl | CH₂CN | H |
| Me | Cl | Cl | CH(Me)CH₂SMe | H |
| Me | Cl | Cl | C(Me)₂CH₂SMe | H |
| Me | Cl | Cl | Me | Me |
| Me | Cl | Br | H | H |
| Me | Cl | Br | Me | H |
| Me | Cl | Br | Et | H |
| Me | Cl | Br | i-Pr | H |
| Me | Cl | Br | t-Bu | H |
| Me | Cl | Br | CH₂CN | H |
| Me | Cl | Br | CH(Me)CH₂SMe | H |
| Me | Cl | Br | C(Me)₂CH₂SMe | H |
| Me | Cl | Br | Me | Me |
| Me | Br | F | H | H |
| Me | Br | F | Me | H |
| Me | Br | F | Et | H |
| Me | Br | F | i-Pr | H |
| Me | Br | F | t-Bu | H |
| Me | Br | F | CH₂CN | H |
| Me | Br | F | CH(Me)CH₂SMe | H |
| Me | Br | F | C(Me)₂CH₂SMe | H |
| Me | Br | F | Me | Me |
| Me | Br | Cl | H | H |
| Me | Br | Cl | Me | H |
| Me | Br | Cl | Et | H |
| Me | Br | Cl | i-Pr | H |
| Me | Br | Cl | t-Bu | H |
| Me | Br | Cl | CH₂CN | H |
| Me | Br | Cl | CH(Me)CH₂SMe | H |
| Me | Br | Cl | C(Me)₂CH₂SMe | H |
| Me | Br | Cl | Me | Me |
| Me | Br | Br | H | H |
| Me | Br | Br | Me | H |
| Me | Br | Br | Et | H |
| Me | Br | Br | i-Pr | H |
| Me | Br | Br | t-Bu | H |
| Me | Br | Br | CH₂CN | H |
| Me | Br | Br | CH(Me)CH₂SMe | H |
| Me | Br | Br | C(Me)₂CH₂SMe | H |
| Me | Br | Br | Me | Me |
| Me | CF₃ | F | H | H |
| Me | CF₃ | F | Me | H |
| Me | CF₃ | F | Et | H |
| Me | CF₃ | F | i-Pr | H |
| Me | CF₃ | F | t-Bu | H |
| Me | CF₃ | F | CH₂CN | H |
| Me | CF₃ | F | CH(Me)CH₂SMe | H |
| Me | CF₃ | F | C(Me)₂CH₂SMe | H |
| Me | CF₃ | F | Me | Me |
| Me | CF₃ | Cl | H | H |
| Me | CF₃ | Cl | Me | H |
| Me | CF₃ | Cl | Et | H |
| Me | CF₃ | Cl | i-Pr | H |
| Me | CF₃ | Cl | t-Bu | H |
| Me | CF₃ | Cl | CH₂CN | H |
| Me | CF₃ | Cl | CH(Me)CH₂SMe | H |
| Me | CF₃ | Cl | C(Me)₂CH₂SMe | H |
| Me | CF₃ | Cl | Me | Me |
| Me | CF₃ | Br | H | H |
| Me | CF₃ | Br | Me | H |
| Me | CF₃ | Br | Et | H |
| Me | CF₃ | Br | i-Pr | H |
| Me | CF₃ | Br | t-Bu | H |
| Me | CF₃ | Br | CH₂CN | H |
| Me | CF₃ | Br | CH(Me)CH₂SMe | H |
| Me | CF₃ | Br | C(Me)₂CH₂SMe | H |
| Me | CF₃ | Br | Me | Me |
| Me | OCF₂H | F | H | H |
| Me | OCF₂H | F | Me | H |
| Me | OCF₂H | F | Et | H |
| Me | OCF₂H | F | i-Pr | H |
| Me | OCF₂H | F | t-Bu | H |
| Me | OCF₂H | F | CH₂CN | H |
| Me | OCF₂H | F | CH(Me)CH₂SMe | H |
| Me | OCF₂H | F | C(Me)₂CH₂SMe | H |
| Me | OCF₂H | F | Me | Me |
| Me | OCF₂H | Cl | H | H |
| Me | OCF₂H | Cl | Me | H |
| Me | OCF₂H | Cl | Et | H |
| Me | OCF₂H | Cl | i-Pr | H |
| Me | OCF₂H | Cl | t-Bu | H |
| Me | OCF₂H | Cl | CH₂CN | H |
| Me | OCF₂H | Cl | CH(Me)CH₂SMe | H |
| Me | OCF₂H | Cl | C(Me)₂CH₂SMe | H |
| Me | OCF₂H | Cl | Me | Me |
| Me | OCF₂H | Br | H | H |
| Me | OCF₂H | Br | Me | H |
| Me | OCF₂H | Br | Et | H |
| Me | OCF₂H | Br | i-Pr | H |
| Me | OCF₂H | Br | t-Bu | H |
| Me | OCF₂H | Br | CH₂CN | H |
| Me | OCF₂H | Br | CH(Me)CH₂SMe | H |
| Me | OCF₂H | Br | C(Me)₂CH₂SMe | H |
| Me | OCF₂H | Br | Me | Me |
| Me | OCH₂CF₃ | F | H | H |
| Me | OCH₂CF₃ | F | Me | H |
| Me | OCH₂CF₃ | F | Et | H |
| Me | OCH₂CF₃ | F | i-Pr | H |
| Me | OCH₂CF₃ | F | t-Bu | H |

TABLE 1-continued

| R¹ | R² | R³ | R⁴ | R⁵ |
|---|---|---|---|---|
| Me | OCH₂CF₃ | F | CH₂CN | H |
| Me | OCH₂CF₃ | F | CH(Me)CH₂SMe | H |
| Me | OCH₂CF₃ | F | C(Me)₂CH₂SMe | H |
| Me | OCH₂CF₃ | F | Me | Me |
| Me | OCH₂CF₃ | Cl | H | H |
| Me | OCH₂CF₃ | Cl | Me | H |
| Me | OCH₂CF₃ | Cl | Et | H |
| Me | OCH₂CF₃ | Cl | i-Pr | H |
| Me | OCH₂CF₃ | Cl | t-Bu | H |
| Me | OCH₂CF₃ | Cl | CH₂CN | H |
| Me | OCH₂CF₃ | Cl | CH(Me)CH₂SMe | H |
| Me | OCH₂CF₃ | Cl | C(Me)₂CH₂SMe | H |
| Me | OCH₂CF₃ | Cl | Me | Me |
| Me | OCH₂CF₃ | Br | H | H |
| Me | OCH₂CF₃ | Br | Me | H |
| Me | OCH₂CF₃ | Br | Et | H |
| Me | OCH₂CF₃ | Br | i-Pr | H |
| Me | OCH₂CF₃ | Br | t-Bu | H |
| Me | OCH₂CF₃ | Br | CH₂CN | H |
| Me | OCH₂CF₃ | Br | CH(Me)CH₂SMe | H |
| Me | OCH₂CF₃ | Br | C(Me)₂CH₂SMe | H |
| Me | OCH₂CF₃ | Br | Me | Me |
| Me | OCF₃ | F | H | H |
| Me | OCF₃ | F | Me | H |
| Me | OCF₃ | F | Et | H |
| Me | OCF₃ | F | i-Pr | H |
| Me | OCF₃ | F | t-Bu | H |
| Me | OCF₃ | F | CH₂CN | H |
| Me | OCF₃ | F | CH(Me)CH₂SMe | H |
| Me | OCF₃ | F | C(Me)₂CH₂SMe | H |
| Me | OCF₃ | F | Me | Me |
| Me | OCF₃ | Cl | H | H |
| Me | OCF₃ | Cl | Me | H |
| Me | OCF₃ | Cl | Et | H |
| Me | OCF₃ | Cl | i-Pr | H |
| Me | OCF₃ | Cl | t-Bu | H |
| Me | OCF₃ | Cl | CH₂CN | H |
| Me | OCF₃ | Cl | CH(Me)CH₂SMe | H |
| Me | OCF₃ | Cl | C(Me)₂CH₂SMe | H |
| Me | OCF₃ | Cl | Me | Me |
| Me | OCF₃ | Br | H | H |
| Me | OCF₃ | Br | Me | H |
| Me | OCF₃ | Br | Et | H |
| Me | OCF₃ | Br | i-Pr | H |
| Me | OCF₃ | Br | t-Bu | H |
| Me | OCF₃ | Br | CH₂CN | H |
| Me | OCF₃ | Br | CH(Me)CH₂SMe | H |
| Me | OCF₃ | Br | C(Me)₂CH₂SMe | H |
| Me | OCF₃ | Br | Me | Me |
| Cl | Cl | F | H | H |
| Cl | Cl | F | Me | H |
| Cl | Cl | F | Et | H |
| Cl | Cl | F | i-Pr | H |
| Cl | Cl | F | t-Bu | H |
| Cl | Cl | F | CH₂CN | H |
| Cl | Cl | F | CH(Me)CH₂SMe | H |
| Cl | Cl | F | C(Me)₂CH₂SMe | H |
| Cl | Cl | F | Me | Me |
| Cl | Cl | Cl | H | H |
| Cl | Cl | Cl | Me | H |
| Cl | Cl | Cl | Et | H |
| Cl | Cl | Cl | i-Pr | H |
| Cl | Cl | Cl | t-Bu | H |
| Cl | Cl | Cl | CH₂CN | H |
| Cl | Cl | Cl | CH(Me)CH₂SMe | H |
| Cl | Cl | Cl | C(Me)₂CH₂SMe | H |
| Cl | Cl | Cl | Me | Me |
| Cl | Cl | Br | H | H |
| Cl | Cl | Br | Me | H |
| Cl | Cl | Br | Et | H |
| Cl | Cl | Br | i-Pr | H |
| Cl | Cl | Br | t-Bu | H |
| Cl | Cl | Br | CH₂CN | H |
| Cl | Cl | Br | CH(Me)CH₂SMe | H |
| Cl | Cl | Br | C(Me)₂CH₂SMe | H |
| Cl | Cl | Br | Me | Me |
| Cl | Br | F | H | H |
| Cl | Br | F | Me | H |
| Cl | Br | F | Et | H |
| Cl | Br | F | i-Pr | H |
| Cl | Br | F | t-Bu | H |
| Cl | Br | F | CH₂CN | H |
| Cl | Br | F | CH(Me)CH₂SMe | H |
| Cl | Br | F | C(Me)₂CH₂SMe | H |
| Cl | Br | F | Me | Me |
| Cl | Br | Cl | H | H |
| Cl | Br | Cl | Me | H |
| Cl | Br | Cl | Et | H |
| Cl | Br | Cl | i-Pr | H |
| Cl | Br | Cl | t-Bu | H |
| Cl | Br | Cl | CH₂CN | H |
| Cl | Br | Cl | CH(Me)CH₂SMe | H |
| Cl | Br | Cl | C(Me)₂CH₂SMe | H |
| Cl | Br | Cl | Me | Me |
| Cl | Br | Br | H | H |
| Cl | Br | Br | Me | H |
| Cl | Br | Br | Et | H |
| Cl | Br | Br | i-Pr | H |
| Cl | Br | Br | t-Bu | H |
| Cl | Br | Br | CH₂CN | H |
| Cl | Br | Br | CH(Me)CH₂SMe | H |
| Cl | Br | Br | C(Me)₂CH₂SMe | H |
| Cl | Br | Br | Me | Me |
| Cl | CF₃ | F | H | H |
| Cl | CF₃ | F | Me | H |
| Cl | CF₃ | F | Et | H |
| Cl | CF₃ | F | i-Pr | H |
| Cl | CF₃ | F | t-Bu | H |
| Cl | CF₃ | F | CH₂CN | H |
| Cl | CF₃ | F | CH(Me)CH₂SMe | H |
| Cl | CF₃ | F | C(Me)₂CH₂SMe | H |
| Cl | CF₃ | F | Me | Me |
| Cl | CF₃ | Cl | H | H |
| Cl | CF₃ | Cl | Me | H |
| Cl | CF₃ | Cl | Et | H |
| Cl | CF₃ | Cl | i-Pr | H |
| Cl | CF₃ | Cl | t-Bu | H |
| Cl | CF₃ | Cl | CH₂CN | H |
| Cl | CF₃ | Cl | CH(Me)CH₂SMe | H |
| Cl | CF₃ | Cl | C(Me)₂CH₂SMe | H |

TABLE 1-continued

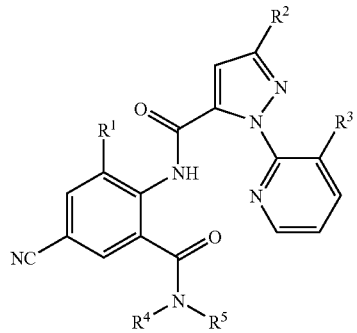

| R¹ | R² | R³ | R⁴ | R⁵ |
|---|---|---|---|---|
| Cl | CF₃ | Cl | Me | Me |
| Cl | CF₃ | Br | H | H |
| Cl | CF₃ | Br | Me | H |
| Cl | CF₃ | Br | Et | H |
| Cl | CF₃ | Br | i-Pr | H |
| Cl | CF₃ | Br | t-Bu | H |
| Cl | CF₃ | Br | CH₂CN | H |
| Cl | CF₃ | Br | CH(Me)CH₂SMe | H |
| Cl | CF₃ | Br | C(Me)₂CH₂SMe | H |
| Cl | CF₃ | Br | Me | Me |
| Cl | OCF₂H | F | H | H |
| Cl | OCF₂H | F | Me | H |
| Cl | OCF₂H | F | Et | H |
| Cl | OCF₂H | F | i-Pr | H |
| Cl | OCF₂H | F | t-Bu | H |
| Cl | OCF₂H | F | CH₂CN | H |
| Cl | OCF₂H | F | CH(Me)CH₂SMe | H |
| Cl | OCF₂H | F | C(Me)₂CH₂SMe | H |
| Cl | OCF₂H | F | Me | Me |
| Cl | OCF₂H | Cl | H | H |
| Cl | OCF₂H | Cl | Me | H |
| Cl | OCF₂H | Cl | Et | H |
| Cl | OCF₂H | Cl | i-Pr | H |
| Cl | OCF₂H | Cl | t-Bu | H |
| Cl | OCF₂H | Cl | CH₂CN | H |
| Cl | OCF₂H | Cl | CH(Me)CH₂SMe | H |
| Cl | OCF₂H | Cl | C(Me)₂CH₂SMe | H |
| Cl | OCF₂H | Cl | Me | Me |
| Cl | OCF₂H | Br | H | H |
| Cl | OCF₂H | Br | Me | H |
| Cl | OCF₂H | Br | Et | H |
| Cl | OCF₂H | Br | i-Pr | H |
| Cl | OCF₂H | Br | t-Bu | H |
| Cl | OCF₂H | Br | CH₂CN | H |
| Cl | OCF₂H | Br | CH(Me)CH₂SMe | H |
| Cl | OCF₂H | Br | C(Me)₂CH₂SMe | H |
| Cl | OCF₂H | Br | Me | Me |
| Cl | OCH₂CF₃ | F | H | H |
| Cl | OCH₂CF₃ | F | Me | H |
| Cl | OCH₂CF₃ | F | Et | H |
| Cl | OCH₂CF₃ | F | i-Pr | H |
| Cl | OCH₂CF₃ | F | t-Bu | H |
| Cl | OCH₂CF₃ | F | CH₂CN | H |
| Cl | OCH₂CF₃ | F | CH(Me)CH₂SMe | H |
| Cl | OCH₂CF₃ | F | C(Me)₂CH₂SMe | H |
| Cl | OCH₂CF₃ | F | Me | Me |
| Cl | OCH₂CF₃ | Cl | H | H |
| Cl | OCH₂CF₃ | Cl | Me | H |
| Cl | OCH₂CF₃ | Cl | Et | H |
| Cl | OCH₂CF₃ | Cl | i-Pr | H |
| Cl | OCH₂CF₃ | Cl | t-Bu | H |
| Cl | OCH₂CF₃ | Cl | CH₂CN | H |
| Cl | OCH₂CF₃ | Cl | CH(Me)CH₂SMe | H |
| Cl | OCH₂CF₃ | Cl | C(Me)₂CH₂SMe | H |
| Cl | OCH₂CF₃ | Cl | Me | Me |
| Cl | OCH₂CF₃ | Br | H | H |
| Cl | OCH₂CF₃ | Br | Me | H |
| Cl | OCH₂CF₃ | Br | Et | H |
| Cl | OCH₂CF₃ | Br | i-Pr | H |
| Cl | OCH₂CF₃ | Br | t-Bu | H |

TABLE 1-continued

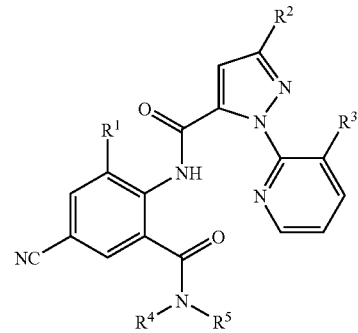

| R¹ | R² | R³ | R⁴ | R⁵ |
|---|---|---|---|---|
| Cl | OCH₂CF₃ | Br | CH₂CN | H |
| Cl | OCH₂CF₃ | Br | CH(Me)CH₂SMe | H |
| Cl | OCH₂CF₃ | Br | C(Me)₂CH₂SMe | H |
| Cl | OCH₂CF₃ | Br | Me | Me |
| Cl | OCF₃ | F | H | H |
| Cl | OCF₃ | F | Me | H |
| Cl | OCF₃ | F | Et | H |
| Cl | OCF₃ | F | i-Pr | H |
| Cl | OCF₃ | F | t-Bu | H |
| Cl | OCF₃ | F | CH₂CN | H |
| Cl | OCF₃ | F | CH(Me)CH₂SMe | H |
| Cl | OCF₃ | F | C(Me)₂CH₂SMe | H |
| Cl | OCF₃ | F | Me | Me |
| Cl | OCF₃ | Cl | H | H |
| Cl | OCF₃ | Cl | Me | H |
| Cl | OCF₃ | Cl | Et | H |
| Cl | OCF₃ | Cl | i-Pr | H |
| Cl | OCF₃ | Cl | t-Bu | H |
| Cl | OCF₃ | Cl | CH₂CN | H |
| Cl | OCF₃ | Cl | CH(Me)CH₂SMe | H |
| Cl | OCF₃ | Cl | C(Me)₂CH₂SMe | H |
| Cl | OCF₃ | Cl | Me | Me |
| Cl | OCF₃ | Br | H | H |
| Cl | OCF₃ | Br | Me | H |
| Cl | OCF₃ | Br | Et | H |
| Cl | OCF₃ | Br | i-Pr | H |
| Cl | OCF₃ | Br | t-Bu | H |
| Cl | OCF₃ | Br | CH₂CN | H |
| Cl | OCF₃ | Br | CH(Me)CH₂SMe | H |
| Cl | OCF₃ | Br | C(Me)₂CH₂SMe | H |
| Cl | OCF₃ | Br | Me | Me |

TABLE 2

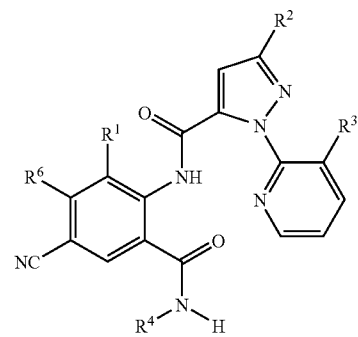

| R¹ | R² | R³ | R⁴ | R⁶ |
|---|---|---|---|---|
| Me | CF₃ | Cl | Me | F |
| Cl | CF₃ | Cl | Me | F |
| Br | CF₃ | Cl | Me | F |
| Me | Cl | Cl | Me | F |
| Cl | Cl | Cl | Me | F |

TABLE 2-continued

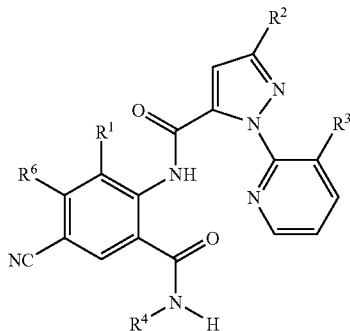

| R¹ | R² | R³ | R⁴ | R⁶ |
|---|---|---|---|---|
| Br | Cl | Cl | Me | F |
| Me | Br | Cl | Me | F |
| Cl | Br | Cl | Me | F |
| Br | Br | Cl | Me | F |
| Me | CF₃ | Cl | i-Pr | F |
| Cl | CF₃ | Cl | i-Pr | F |
| Br | CF₃ | Cl | i-Pr | F |
| Me | Cl | Cl | i-Pr | F |
| Cl | Cl | Cl | i-Pr | F |
| Br | Cl | Cl | i-Pr | F |
| Me | Br | Cl | i-Pr | F |
| Cl | Br | Cl | i-Pr | F |
| Br | Br | Cl | i-Pr | F |
| Me | CF₃ | Cl | Me | Cl |
| Cl | CF₃ | Cl | Me | Cl |
| Br | CF₃ | Cl | Me | Cl |
| Me | Cl | Cl | Me | Cl |
| Cl | Cl | Cl | Me | Cl |
| Br | Cl | Cl | Me | Cl |
| Me | Br | Cl | Me | Cl |
| Cl | Br | Cl | Me | Cl |
| Br | Br | Cl | Me | Cl |
| Me | CF₃ | Cl | i-Pr | Cl |
| Cl | CF₃ | Cl | i-Pr | Cl |
| Br | CF₃ | Cl | i-Pr | Cl |
| Me | Cl | Cl | i-Pr | Cl |
| Cl | Cl | Cl | i-Pr | Cl |
| Br | Cl | Cl | i-Pr | Cl |
| Me | Br | Cl | i-Pr | Cl |
| Cl | Br | Cl | i-Pr | Cl |
| Br | Br | Cl | i-Pr | Cl |

TABLE 3

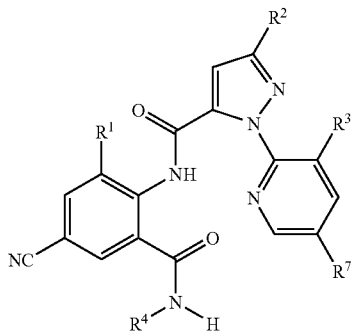

| R¹ | R² | R³ | R⁴ | R⁷ |
|---|---|---|---|---|
| Me | CF₃ | F | Me | F |
| Cl | CF₃ | F | Me | F |
| Br | CF₃ | F | Me | F |
| Me | Cl | F | Me | F |
| Cl | Cl | F | Me | F |
| Br | Cl | F | Me | F |

TABLE 3-continued

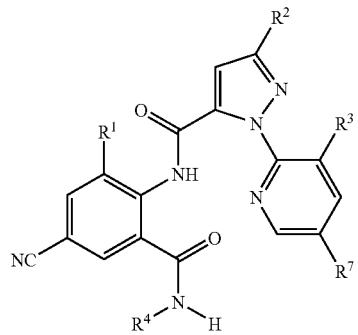

| R¹ | R² | R³ | R⁴ | R⁷ |
|---|---|---|---|---|
| Me | Br | F | Me | F |
| Cl | Br | F | Me | F |
| Br | Br | F | Me | F |
| Me | CF₃ | F | i-Pr | F |
| Cl | CF₃ | F | i-Pr | F |
| Br | CF₃ | F | i-Pr | F |
| Me | Cl | F | i-Pr | F |
| Cl | Cl | F | i-Pr | F |
| Br | Cl | F | i-Pr | F |
| Me | Br | F | i-Pr | F |
| Cl | Br | F | i-Pr | F |
| Br | Br | F | i-Pr | F |
| Me | CF₃ | Cl | Me | Cl |
| Cl | CF₃ | Cl | Me | Cl |
| Br | CF₃ | Cl | Me | Cl |
| Me | Cl | Cl | Me | Cl |
| Cl | Cl | Cl | Me | Cl |
| Br | Cl | Cl | Me | Cl |
| Me | Br | Cl | Me | Cl |
| Cl | Br | Cl | Me | Cl |
| Br | Br | Cl | Me | Cl |
| Me | CF₃ | Cl | i-Pr | Cl |
| Cl | CF₃ | Cl | i-Pr | Cl |
| Br | CF₃ | Cl | i-Pr | Cl |
| Me | Cl | Cl | i-Pr | Cl |
| Cl | Cl | Cl | i-Pr | Cl |
| Br | Cl | Cl | i-Pr | Cl |
| Me | Br | Cl | i-Pr | Cl |
| Cl | Br | Cl | i-Pr | Cl |
| Br | Br | Cl | i-Pr | Cl |

The invention described herein relates to a method of controlling or prevention of infestations of flies on an animal by administering to the animal an insecticidally effective amount of a compound of Formula 1.

Administration of Compounds of the Invention

The compounds of Formula 1 of this invention can be applied to homeothermic animals in need of treatment or prevention of ectoparasitic infestation. Particularly contemplated are important agronomic or companion animals such cattle, sheep, horses, goats, pigs, llamas, camels, water buffalo, donkeys, rabbits, fallow deer, reindeer, minks, chinchillas, ferrets, raccoons, chickens, geese, turkeys, ducks, dogs, cats, mice rats, or the like. Herd animals such as cattle, sheep, goats, horses, donkeys, camels, pigs, reindeer, caribou and buffalo may be treated. Humans may also be treated.

Any of the compounds of the present invention, or a suitable combination of such compounds, may be administered directly to the animal subject and/or indirectly by applying it to the local environment in which the animal dwells (such as bedding, enclosures, or the like). Direct administration includes contacting the skin, fur or feathers of a subject animal with the compounds, or by feeding or injecting the compounds into the animal.

Topical Administration

When topical administration is required, the administration to the animal or the environment can be accomplished by way of non limiting example, by sprays, dusts, pour on treatments and controlled-release devices, such as ear tags and tapes, neck collars, ear tags, tail bands, limb bands or halters which comprise compounds or compositions comprising compounds of Formula 1. In addition to sprays and pour on treatments, application may be by other forms of topical administration, for example, in the form of immersion or dipping, washing, coating with powder, or application to a small area of the animal.

Application of the compositions according to the invention to the animals to be treated is done topically via solutions, emulsions, suspensions, (drenches), powders, and pour-on formulations.

The pour-on or spot-on method consists in applying the compound of Formula 1 to a specific location of the skin or coat, advantageously to the neck or backbone of the animal. This takes place e.g. by applying a swab or spray of the pour-on or spot-on formulation to a relatively small area of the coat, from where the active substance is dispersed almost automatically over wide areas of the fur owing to the spreading nature of the components in the formulation and assisted by the animal's movements.

Importantly the compounds of Formula 1 may be indirectly applied to an animal by applying it to the local environment in which the animal dwells (such as bedding, enclosures, or the like). Effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of pest control.

The invention notably provides a process for controlling the hematophageous ectoparasites of small mammals, and in particular cats and dogs, is treated by locally depositing on the skin, preferably localized over a small surface area (spot-on application) It is preferable for the treatment according to the invention to be carried out every one, two or, three months on cats and dogs.

The compounds of the present invention may be administered in a controlled release form, e.g., in a subcutaneous slow release formulation, or in the form of a controlled release device affixed to an animal such as a fleacollar. Collars for the controlled release of an insecticide agent for long term protection against flea infestation in a companion animal are art-known, and are described, for example, by U.S. Pat. No. 3,852,416, U.S. Pat. No. 4,224,901, U.S. Pat. No. 5,555,848 and U.S. Pat. No. 5,184,573.

Large animals particularly herd animals are efficiently treated by a variety of methods well known in the art.

Whole-animal sprays provide rapid relief from fly pressure. Animal sprays are applied either as a dilute coarse spray, often applied under high pressure to soak the skin, or as a fine low-volume, more concentrated mist.

Self-applicating devices include back rubber covered with an absorbent material treated with an insecticide-oil solution, or dust bags filled with an insecticidal dust. Back rubbers and dustbags should be placed in gateways, near water and feed source, and in other areas where animals will make frequent contact with them.

Controlled-release ear tags and tapes are generally very effective for fly control in certain farm areas.

Pour-on treatments involves the application of an insecticide along the backline of the animal at a prescribed dosage of topical products. The pour-on or spot-on method is especially advantageous for use on herd animals such as cattle, horses, sheep or pigs, in which it is difficult or time-consuming to treat all the animals by more labor intensive methods of administration.

Oral Administration

Compounds of the present invention can be delivered by ingestion to the animal to be protected After ingestion by the animal to be protected, parasiticidally effective concentrations of compounds of the invention in the bloodstream protect the treated animal from blood-sucking pests such as fleas, ticks and lice.

Parenteral Administration

The compound of Formula 1 may be administered by parenterally including by injection. Injections may be intravenous, intramuscular or subcutaneous.

Compositions of the Invention

The compounds of the invention may be applied or administered alone but are typically formulated into a veterinary or pharmaceutical composition. The compounds are prepared or formulated into compositions in a known manner, for example by extending the active compounds with solvents and/or carriers, if appropriate using emulsifiers and/or dispersing agents; if, for example, water is used as the diluent, organic solvents can, if appropriate, be used as auxiliary solvents.

Typically a parasiticidal composition according to the present invention comprises a mixture of a compound of Formula 1 with one or more pharmaceutically or veterinarily acceptable carriers comprising excipients and auxiliaries selected with regard to the intended route of administration (e.g., oral, topical or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an ectoparasitic pest comprising a parasitically effective amount of a compound of the invention and at least one carrier.

Formulations for topical administration are typically in the form of a powder, cream, suspension, spray, emulsion, foam, paste, aerosol, ointment, salve or gel. A topical formulation may be a water-soluble solution, which can be in the form of a concentrate that is diluted before use. Parasiticidal compositions suitable for topical administration typically comprise a compound of the present invention and one or more topically suitable carriers.

In applications of a parasiticidal composition topically to the exterior of an animal as a line or spot (i.e. "spot-on" treatment), the active ingredient migrates over the surface of the animal to cover most or all of its external surface area. As a result, the treated animal is particularly protected from invertebrate pests that feed off the epidermis of the animal such as ticks, fleas and lice. Therefore formulations for topical localized administration often comprise at least one organic solvent to facilitate transport of the active ingredient over the skin and/or penetration into the epidermis of the animal. Pour-on or spot-on formulations suitably contain carriers, which promote rapid dispersement over the skin surface or in the coat of the host animal, and are generally regarded as spreading oils. Suitable carriers are e.g. oily solutions; alcoholic and isopropanolic solutions such as solutions of 2-octyldodecanol or oleyl alcohol; solutions in esters of monocarboxylic acids, such as isopropyl myristate, isopropyl palmitate, lauric acid oxalate, oleic acid oleyl ester, oleic acid decyl ester, hexyl laurate, oleyl oleate, decyl oleate, capric acid esters of saturated fat alcohols of chain length $C_{12}$-$C_{18}$;

solutions of esters of dicarboxylic acids, such as dibutyl phthalate, diisopropyl isophthalate, adipic acid diisopropyl ester, di-n-butyl adipate or also solutions of esters of aliphatic acids, e.g. glycols. It may be advantageous for a dispersing agent to be additionally present, such as one known from the pharmaceutical or cosmetic industry. Examples are 2-pyrrolidone, 2-(N-alkyl)pyrrolidone, acetone, polyethylene glycol and the ethers and esters thereof, propylene glycol or synthetic triglycerides.

The oily solutions include e.g. vegetable oils such as olive oil, groundnut oil, sesame oil, pine oil, linseed oil or castor oil. The vegetable oils may also be present in epoxidised form. Paraffins and silicone oils may also be used.

It may be advantageous for a crystallization inhibitor or a dispersant known from the pharmaceutical or cosmetic industry also to be present.

A pour-on or spot-on formulation generally contains 1 to 20% by weight of a compound of Formula 1, 0.1 to 50% by weight of dispersing agent and 45 to 98.9% by weight of solvent.

The compositions for spot-on application can advantageously comprise: (a) a crystallization inhibitor, in particular one which is present in a proportion of from 1 to 20% (w/v), preferably from 5 to 15%, this inhibitor satisfying the test according to which: 0.3 ml of 10% (w/v) of a compound of Formula 1 in the solvent defined in (c) below, along with 10% of this inhibitor, are deposited on a glass slide at 20° C. for 24 hours, after which it is observed with the naked eye that there are few or no crystals, in particular fewer than 10 crystals, preferably 0 crystals on the glass slide, (b) an organic solvent having a dielectric constant of between 10 and 35, preferably of between 20 and 30, the content of this solvent (b) in the overall composition preferably representing the difference to make the composition up to 100%, (c) an organic cosolvent having a boiling point of below 100° C., preferably of below 80° C., and having a dielectric constant of between 10 and 40, preferably of between 20 and 30; this cosolvent may advantageously be present in the composition in a (c)/b) weight/weight (w/w) ratio of between 1/15 and 1/2. The solvent is volatile, so as to serve in particular as a drying promoter, and is miscible with water and/or with the solvent (b).

A pour-on formulation may also be prepared for control of parasites in an animal of agricultural worth. The pour-on formulations of this invention can be in the form of a liquid, powder, emulsion, foam, paste, aerosol, ointment, salve or gel. Typically, the pour-on formulation is liquid. These pour-on formulations can be effectively applied to sheep, cattle, goats, other ruminants, camelids, pigs and horses. The pour-on formulation is typically applied by pouring in one or several lines or in a spot-on the dorsal midline (back) or shoulder of an animal. More typically, the formulation is applied by pouring it along the back of the animal, following the spine. The formulation can also be applied to the animal by other conventional methods, including wiping an impregnated material over at least a small area of the animal, or applying it using a commercially available applicator, by means of a syringe, by spraying or by using a spray race. The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The pour-on formulations include a carrier and can also include one or more additional ingredients. Examples of suitable additional ingredients are stabilizers such as antioxidants, spreading agents, preservatives, adhesion promoters, active solubilisers such as oleic acid, viscosity modifiers, UV blockers or absorbers, and colourants. Surface active agents, including anionic, cationic, non-ionic and ampholytic surface active agents, can also be included in these formulations.

The formulations of this invention often include an antioxidant, such as BHT (butylated hydroxytoluene). The antioxidant is generally present in amounts of at 0.005-5% (w/v) a proportion of from 0.005 to 1% (w/v) is often used, with 0.01 to 0.05% often preferred.

The compositions according to the invention intended for pets, in particular cats and dogs, are generally applied by being deposited onto the skin ("spot-on" or "pour-on" application); this is generally a localized application over a surface area of less than 10 cm$^2$, especially of between 5 and 10 cm$^2$, in particular at two points and preferably localized between the animal's shoulders. Once deposited, the composition diffuses, in particular over the animal's entire body, and then dries without crystallizing or modifying the appearance (in particular absence of any whitish deposit or dusty appearance) or the feel of the fur. The compositions for spot-on application according to the invention are particularly advantageous owing to their efficacy, their speed of action and the pleasant appearance of the animal's fur after application and drying.

As organic solvent (b) which can be used in the invention, mention may be made in particular of: acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol and diethyl phthalate, or a mixture of at least two of these solvents. As crystallization inhibitor (a) which can be used in the invention, mention may be made in particular of: polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, acrylic derivatives such as methacrylates and the like, anionic surfactants such as alkaline stearates, in particular sodium, potassium or ammonium stearate; calcium stearate; triethanolamine stearate; sodium abietate; alkyl sulphates, in particular sodium lauryl sulphate and sodium cetyl sulphate; sodium dodecylbenzenesulphonate, sodium dioctylsulphosuccinate; fatty acids, in particular those derived from coconut oil, cationic surfactants such as water-soluble quaternary ammonium salts of formula N$^+$R'R"R'"R"",Y— in which the radicals R are optionally hydroxylated hydrocarbon radicals and Y$^-$ is an anion of a strong acid such as the halide, sulphate and sulphonate anions; cetyltrimethylammonium bromide is among the cationic surfactants which can be used, amine salts of formula N$^+$R'R"R'" in which the radicals R are optionally hydroxylated hydrocarbon radicals; octadecylamine hydrochloride is among the cationic surfactants which can be used, nonionic surfactants such as optionally polyoxyethylenated sorbitan esters, in particular polysorbate 80, polyoxyethylenated alkyl ethers; polyethylene glycol stearate, polyoxyethylenated derivatives of castor oil, polyglycerol esters, polyoxyethylenated fatty alcohols, polyoxyethylenated fatty acids, copolymers of ethylene oxide and propylene oxide, amphoteric surfactants such as substituted lauryl compounds of betaine, or preferably a mixture of at least two of these crystallization inhibitors.

In a particularly preferred manner, a crystallization inhibitor couple, namely the combination of a film-forming agent of polymeric type and a surfactant, will be used. These agents will be chosen in particular from the compounds mentioned as crystallization inhibitor b).

Among the film-forming agents of polymeric type which are particularly advantageous, mention may be made of: the various grades of polyvinylpyrrolidone, polyvinyl alcohols, and copolymers of vinyl acetate and vinylpyrrolidone. As regards the surfactants, mention will be made most particularly of nonionic surfactants, preferably polyoxyethylenated sorbitan esters and in particular the various grades of polysorbate, for example polysorbate 80.

The film-forming agent and the surfactant may be incorporated, in particular, in similar or identical amounts within the limit of the total amounts of crystallization inhibitor mentioned elsewhere.

The couple thus produced ensures the objectives of absence of crystallization on the hairs and maintenance of the cosmetic appearance of the coat in a note-worthy manner, that is to say without any tendency towards stickiness or to a sticky appearance, despite the high concentration of active material. As cosolvent (c), mention may be made in particular of: absolute ethanol, isopropanol, methanol.

As antioxidant, standard agents are used in particular, such as: butylhydroxyanisole, butylhydroxytoluene, ascorbic acid, sodium metabisulphite, propyl gallate and sodium thiosulphate, or a mixture of not more than two of these agents.

The compositions for spot-on application according to the invention are usually prepared by simple mixing of the constituents as defined earlier; advantageously, to begin with, the active material is mixed in the main solvent and the other ingredients or adjuvants are then added.

The volume applied may be from about 0.3 to 5 ml, preferably about 0.5 ml for cats, and from about 0.3 to 3 ml for dogs, according to the weight of the animal.

The composition according to the invention may be in the form of a concentrated emulsion, suspension or solution for spot-on application to a small area of the animal's skin, generally between the two shoulders (spot-on type solution). In a another aspect of the invention forms of solution or suspension to be sprayed, forms of solution, suspension or emulsion to be poured or spread onto the animal (pour-on type solution) an oil, a cream, an ointment or any other fluid formulation for topical administration may be provided.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used.

The compounds of Formula 1 are generally present in the compositions in concentrations of 0.1 to 95 percent by weight, preferably 0.5 to 90 percent by weight. Preparations which are intended for direct application contain the active compound according to the invention in concentrations of between 0.001 and 5 percent by weight, preferably 0.005 to 3 percent by weight.

Dosages may range from 0.0001 mg/kg of animal body weight to about 1000 mg/kg. of the compound of Formula 1. Sometimes dosages may be from 0.1 mg/kg of animal body weight to about 200 mg/kg. Often times it would be advantageous to administer amounts of about 0.01 to about 100 mg or between 0.02 to about 50 mg/kg. and frequently between 0.1 and 75 mg/kg. Preferably, the treatment is carried out so as to administer to the animal a dose of from 0.1 to 40 mg/kg and in particular from 1 to 30 mg/kg. Administration may be given as a single dose or intermittent in time and may be administered daily, weekly, monthly, bimonthly or quarterly in order to achieve effective results in order to achieve effective results.

Nevertheless it can at times be necessary to deviate from the amounts mentioned, and in particular to do so in accordance with the body weight of the test animal and/or the method of application, but also because of the species of animal and its individual behavior towards the medicament, or the nature of the formulation of the latter and the time or interval at which it is administered. Thus it can suffice in some cases to manage with less than the above mentioned minimum amount while in other cases the upper limit mentioned must be exceeded. Where substantial amounts are applied, it can be advisable to divide these into several individual administrations over the course of the day. The general sense of the other statements made above also applies.

For parenteral administration including intravenous, intramuscular and subcutaneous injection, a compound of the present invention can be formulated in suspension, solution or emulsion in oily or aqueous vehicles, and may contain adjuncts such as suspending, stabilizing and/or dispersing agents. The compounds of the present invention may also be formulated for bolus injection or continuous infusion. Pharmaceutical compositions for injection include aqueous solutions preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the compounds of the present invention may also be formulated as a depot preparation. Such long acting formulations may be administered by implantation (for example, subcutaneously or intramuscularly) or by intramuscular or subcutaneous injection. The compounds of the present invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the compounds of the present invention can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

Compounds of the present invention can be delivered by ingestion to the animal to be protected. After ingestion by the animal to be protected, parasiticidally effective concentrations of compounds of the invention in the bloodstream protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a compound of the invention, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, a compound of the present invention can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry. These additives can include, for example, vitamins, antibiotics, chemotherapeutics, bacteriostats, fungistats, coccidiostats and hormones.

The compounds of Formula 1 are generally present in the compositions in concentrations of 0.1 to 95 percent by weight, preferably 0.5 to 90 percent by weight. Preparations which are intended for direct application contain the active compound according to the invention in concentrations of between 0.001 and 5 percent by weight, preferably 0.005 to 3 percent by weight.

Dosages may range from 0.0001 mg/kg of animal body weight to about 1000 mg/kg. of the compound of Formula 1. Sometimes dosages may be from 0.1 mg/kg of animal body weight to about 200 mg/kg. Often times it would be advantageous to administer amounts of about 0.01 to about 100 mg or between 0.02 to about 50 mg/kg. and frequently between 0.1 and 75 mg/kg. Preferably, the treatment is carried out so as to administer to the animal a dose of from 0.1 to 40 mg/kg and in particular from 1 to 30 mg/kg. Administration may be given as a single dose or intermittent in time and may be administered daily, weekly, monthly, bimonthly or quarterly in order to achieve effective results in order to achieve effective results.

Nevertheless it can at times be necessary to deviate from the amounts mentioned, and in particular to do so in accordance with the body weight of the test animal and/or the method of application, but also because of the species of animal and its individual behavior towards the medicament, or the nature of the formulation of the latter and the time or interval at which it is administered. Thus it can suffice in some cases to manage with less than the above mentioned minimum amount while in other cases the upper limit mentioned must be exceeded. Where substantial amounts are applied, it can be advisable to divide these into several individual administrations over the course of the day. The general sense of the other statements made above also applies.

The Compositions of the Invention May Comprise Additional Active Compounds:

It is contemplated that additional biologically active compounds may be administered at the same time or separately over time to obtain broader spectrum of parasitic control. Such additional biologically active compounds may be packaged together with the compound of Formula 1 as a kit. For convenience sake such additional biologically active compounds may be formulated into the same composition containing the compound of Formula 1 and are selected both with respect to the parasites needing control as well as the suitability of the compound in the mode of administration (oral, parenteral, topical etc.) Therefore the present invention contemplates the use of compositions characterised in that they contain, in addition to a compound of Formula 1, further auxiliaries and/or active compounds, such as additional biologically active compounds, disinfectants (I the case of topical application) or antibiotics may be admixed to the formulations, or the ready-to-use solutions, in addition to the customary solid or liquid extenders, diluents and/or surface-active agents.

Of note are additional biologically active compounds or agents selected from art-known anthelmintics, such as, for example, avermectins (e.g. ivermectin, moxidectin, milbemycin), benzimidazoles (e.g. albendazole, triclabendazole), salicylanilides (e.g. closantel, oxyclozanide), substituted phenols (e.g. nitroxynil), pyrimidines (e.g. pyrantel), imidazothiazoles (e.g. levamisole) and praziquantel.

Other biologically active compounds or agents useful in the compositions of the present invention can be selected from Insect Growth Regulators (IGRs) and Juvenile Hormone Analogues (JHAs) such as diflubenzuron, triflumuron, fluazuron, cyromazine, methoprene, etc., thereby providing both initial and sustained control of parasites (at all stages of insect development, including eggs) on the animal subject, as well as within the environment of the animal subject.

The compounds of Formula 1 according to the invention may be used alone or in combination with other biocides. They may be combined with pesticides having the same sphere of activity e.g. to increase activity, or with substances having another sphere of activity e.g. to broaden the range of activity. It can also be sensible to add so-called repellents. If the range of activity is to be extended to endoparasites, e.g. wormers, the compounds of Formula 1 are suitably combined with substances having endoparasitic properties. Of course, they can also be used in combination with antibacterial compositions.

Preferred groups of combination partners and especially preferred combination partners are named in the following, whereby combinations may contain one or more of these partners in addition to a compound of Formula 1.

Suitable partners in the mixture may be biocides, e.g. the insecticides and acaricides with a varying mechanism of activity, which are named in the following and have been known to the person skilled in the art for a long time, e.g. chitin synthesis inhibitors, growth regulators; active ingredients which act as juvenile hormones; active ingredients which act as adulticides; broad-band insecticides, broad-band acaricides and nematicides; and also the well known anthelminthics and insect- and/or acarid-deterring substances, and also repellents or detachers.

Examples of such biologically active compounds include but are not restricted to the following: Organophosphates, a class which are generally know to be inhibitors of acetyl cholinesterase: acephate, azamethiphos, azinphos-ethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemeton-methyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion.

Carbamates, a class which are generally known to be inhibitors of acetyl cholinesterase: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5 methyl-m-cumenylbutyryl(methyl) carbamate, oxamyl, pirimicarb, propoxur, thiodicarb, thiofanox, triazamate, UC-51717 Pyrethroids, a class which are generally known to be modulators of sodium channels: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, 8 cyfluthrin, cyfluthrin, oc-cypermethrin, 8-cypermethrin, bioallethrin, bioallethrin ((S)—I cyclopentylisomer), bioresmethrin, bifenthrin, NCI-85193, cycloprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, \-cyhalothrin, permethrin, phenothrin, prallethrin, pyrethrins (natural products), resmethrin, tetramethrin, transfluthrin, thetacypermethrin, silafluofen, T-fluvalinate, tefluthrin, tralomethrin, Zeta-cypermethrin.

Arthropod growth regulators including: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone agonists/disruptors: halofenozide, methoxyfenozide, tebufenozide; c) juvenoid hormone mimcs: pyriproxyfen, methoprene, fenoxycarb; d) lipid biosynthesis inhibitors: spirodiclofen. Other antiparasitics: acequinocyl, amitraz, AKD-1022, ANS-118, azadirachtin, *Bacillus thuringiensis*, bensultap, bifenazate, binapacryl, bromopropylate, BTG-504, I BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, Sl-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, Yl-5301 Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifioxystrobin, triticonazole, validamycin, vinclozin Biological agents: *Bacillus thuringiensis* ssp alzawai, kurstaki, *Bacillus thuringiensis* delta endotoxin, baculovirus, entomopathogenic bacteria, virus and fungi Bactericides: chlortetracycline, oxytetracycline, streptomycin, Additional more specific examples of partner insecticides and acaricides are listed below:

| Compound | Class |
|---|---|
| Compound | Class |
| Abamectin | macrocyclic lactones |
| AC 303 630 | energy production modulator |
| Acephate | acetyl cholinesterase inhibitor |
| Acrinathin | sodium channel modulator |
| Alanycarb | acetyl cholinesterase inhibitor |
| Aldicarb | acetyl cholinesterase inhibitor |
| alpha.-Cypermethrin | sodium channel modulator |
| Alphamethrin | sodium channel modulator |
| Amitraz | octopamine receptor ligand |
| Avermectin | macrocyclic lactones |
| Azinphos A | acetyl cholinesterase inhibitor |
| Azinphos M | acetyl cholinesterase inhibitor |
| Azinphos-methyl | acetyl cholinesterase inhibitor |
| Azocyclotin | oxidative phosphorylation inhibitor |
| *Bacillus subtil.* toxin | |
| Bendiocarb | acetyl cholinesterase inhibitor |
| Benfuracarb | acetyl cholinesterase inhibitor |
| Bensultap | nicotinic acetylcholine agonist/antagonist |
| beta.-Cyfluthrin | sodium channel modulator |
| Bifenthrin | sodium channel modulator |
| Brofenprox | sodium channel modulator |
| Bromophos A | acetyl cholinesterase inhibitor |
| Bufencarb | acetyl cholinesterase inhibitor |
| Buprofezin | chitin synthesis inhibitor |
| Butocarboxin | acetyl cholinesterase inhibitor |
| Cadusafos | acetyl cholinesterase inhibitor |
| Carbaryl | acetyl cholinesterase inhibitor |
| Carbofuran | acetyl cholinesterase inhibitor |
| Carbophenthion | acetyl cholinesterase inhibitor |
| Cartap | nicotinic acetylcholine agonist/antagonist |
| Chloethocarb | acetyl cholinesterase inhibitor |
| Chlorethoxyfos | acetyl cholinesterase inhibitor |
| Chlorfenapyr | oxidative phosphorylation inhibitor |
| Chlorfluazuron | chitin synthesis inhibitor |
| Chlormephos | acetyl cholinesterase inhibitor |
| Chlorpyrifos | acetyl cholinesterase inhibitor |
| Cis-Resmethrin | sodium channel modulator |
| Clofentezine | |

| Compound | Class |
|---|---|
| Cyanophos | acetyl cholinesterase inhibitor |
| Cycloprothrin | sodium channel modulator |
| Cyfluthrin | sodium channel modulator |
| Cyhexatin | oxidative phosphorylation inhibitor |
| D 2341 (bifenazate) | |
| Deltamethrin | sodium channel modulator |
| Demeton M | acetyl cholinesterase inhibitor |
| Demeton S | acetyl cholinesterase inhibitor |
| Demeton-S-methyl | acetyl cholinesterase inhibitor |
| Dichlofenthion | acetyl cholinesterase inhibitor |
| Dicliphos | acetyl cholinesterase inhibitor |
| Diethion | acetyl cholinesterase inhibitor |
| Diflubenzuron | chitin synthesis inhibitor |
| Dimethoate | acetyl cholinesterase inhibitor |
| Dimethylvinphos | acetyl cholinesterase inhibitor |
| Dioxathion | acetyl cholinesterase inhibitor |
| Doramectin | macrocyclic lactones |
| DPX-MP062 (indoxacarb) | sodium channel modulator |
| Edifenphos | acetyl cholinesterase inhibitor |
| Emamectin | macrocyclic lactones |
| Endosulfan | gaba-gated chloride channel antagonist |
| Eprinomectin | macrocyclic lactones |
| Esfenvalerate | sodium channel modulator |
| Ethiofencarb | acetyl cholinesterase inhibitor |
| Ethion | acetyl cholinesterase inhibitor |
| Ethofenprox | sodium channel modulator |
| Ethoprophos | acetyl cholinesterase inhibitor |
| Etrimphos | acetyl cholinesterase inhibitor |
| Fenamiphos | acetyl cholinesterase inhibitor |
| Fenazaquin | mitochondrial electron transport inhibitor |
| Fenbutatin oxide | oxidative phosphorylation inhibitor |
| Fenitrothion | acetyl cholinesterase inhibitor |
| Fenobucarb (BPMC) | acetyl cholinesterase inhibitor |
| Fenothiocarb | acetyl cholinesterase inhibitor |
| Fenoxycarb | juvenile hormone mimic |
| Fenpropathrin | sodium channel modulator |
| Fenpyrad | mitochondrial electron transport inhibitor |
| Fenpyroximate | mitochondrial electron transport inhibitor |
| Fenthion | acetyl cholinesterase inhibitor |
| Fenvalerate | sodium channel modulator |
| Fipronil | gaba-gated chloride channel antagonist |
| Fluazinam | oxidative phosphorylation uncoupler |
| Fluazuron | chitin synthesis inhibitor |
| Flucycloxuron | chitin synthesis inhibitor |
| Flucythrinate | sodium channel modulator |
| Flufenoxuron | chitin synthesis inhibitor |
| Flufenprox | sodium channel modulator |
| Fonophos | acetyl cholinesterase inhibitor |
| Formothion | acetyl cholinesterase inhibitor |
| Fosthiazate | acetyl cholinesterase inhibitor |
| HCH | gaba-gated chloride channel antagonist |
| Heptenophos | acetyl cholinesterase inhibitor |
| Hexaflumuron | chitin synthesis inhibitor |
| Hexythiazox | |
| Hydroprene | juvenile hormone mimic |
| Imidacloprid | nicotinic acetylcholine agonist/antagonist |
| insect-active fungi | |
| insect-active nematodes | |
| insect-active viruses | |
| Iprobenfos | acetyl cholinesterase inhibitor |
| Isofenphos | acetyl cholinesterase inhibitor |
| Isoprocarb | acetyl cholinesterase inhibitor |
| Isoxathion | acetyl cholinesterase inhibitor |
| Ivermectin | chloride channel activator |
| lambda.-Cyhalothrin | sodium channel modulator |
| Lufenuron | chitin synthesis inhibitor |
| Malathion | acetyl cholinesterase inhibitor |
| Mecarbam | acetyl cholinesterase inhibitor |
| Mesulfenphos | acetyl cholinesterase inhibitor |
| Metaldehyd | |
| Methamidophos | acetyl cholinesterase inhibitor |
| Methiocarb | acetyl cholinesterase inhibitor |
| Methomyl | acetyl cholinesterase inhibitor |
| Methoprene | juvenile hormone mimic |
| Metolcarb | acetyl cholinesterase inhibitor |
| Mevinphos | acetyl cholinesterase inhibitor |
| Milbemectin | macrocyclic lactones |
| Moxidectin | macrocyclic lactones |
| Naled | acetyl cholinesterase inhibitor |
| NI-25, Acetamiprid | nicotinic acetylcholine agonist/antagonist |
| Nitenpyram | nicotinic acetylcholine agonist/antagonist |
| Nodulisporic acid/derivatives | macrocyclic lactones |
| Omethoat | acetyl cholinesterase inhibitor |
| Oxamyl | acetyl cholinesterase inhibitor |
| Oxydemethon M | acetyl cholinesterase inhibitor |
| Oxydeprofos | acetyl cholinesterase inhibitor |
| Parathion | acetyl cholinesterase inhibitor |
| Parathion-methyl | acetyl cholinesterase inhibitor |
| Permethrin | sodium channel modulator |
| Phenthoate | acetyl cholinesterase inhibitor |
| Phorat | acetyl cholinesterase inhibitor |
| Phosalone | acetyl cholinesterase inhibitor |
| Phosmet | acetyl cholinesterase inhibitor |
| Phoxim | acetyl cholinesterase inhibitor |
| Pirimicarb | acetyl cholinesterase inhibitor |
| Pirimiphos A | acetyl cholinesterase inhibitor |
| Pirimiphos M | acetyl cholinesterase inhibitor |
| Promecarb | acetyl cholinesterase inhibitor |
| Propaphos | acetyl cholinesterase inhibitor |
| Propoxur | acetyl cholinesterase inhibitor |
| Prothiofos | acetyl cholinesterase inhibitor |
| Prothoat | acetyl cholinesterase inhibitor |
| Pyrachlophos | acetyl cholinesterase inhibitor |
| Pyradaphenthion | acetyl cholinesterase inhibitor |
| Pyresmethrin | sodium channel modulator |
| Pyrethrim | sodium channel modulator |
| Pyridaben | mitochondrial electron transport inhibitor |
| Pyrimidifen | mitochondrial electron transport inhibitor |
| Pyriproxyfen | juvenile hormone mimic |
| RH 5992 | ecdysone agonist |
| RH-2485 | ecdysone agonist |
| Salithion | acetyl cholinesterase inhibitor |
| selamectin | macrocyclic lactones |
| Silafluofen | sodium channel modulator |
| Spinosad | nicotinic acetylcholine activator |
| Sulfotep | acetyl cholinesterase inhibitor |
| Sulprofos | acetyl cholinesterase inhibitor |
| Tebufenozide | ecdysone agonist |
| Tebufenpyrad | mitochondrial electron transport inhibitor |
| Tebupirimphos | acetyl cholinesterase inhibitor |
| Teflubenzuron | chitin synthesis inhibitor |
| Tefluthrin | sodium channel modulator |
| Temephos | acetyl cholinesterase inhibitor |
| Terbufos | acetyl cholinesterase inhibitor |
| Tetrachlorvinphos | acetyl cholinesterase inhibitor |
| Thiafenox | |
| Thiodicarb | acetyl cholinesterase inhibitor |
| Thiofanox | acetyl cholinesterase inhibitor |
| Thionazin | acetyl cholinesterase inhibitor |
| Thuringiensin | |
| Tralomethrin | sodium channel modulator |
| Triarathen | |
| Triazamate | acetyl cholinesterase inhibitor |
| Triazophos | acetyl cholinesterase inhibitor |
| Trichlorfon | acetyl cholinesterase inhibitor |
| Triflumuron | chitin synthesis inhibitor |
| Trimethacarb | acetyl cholinesterase inhibitor |
| Vamidothion | acetyl cholinesterase inhibitor |
| XMC (3,5,-Xylyl-methylcarbamate) | acetyl cholinesterase inhibitor |
| Xylylcarb | acetyl cholinesterase inhibitor |
| YI 5301/5302 | |
| zeta.-Cypermethrin | sodium channel modulator |
| Zetamethrin | sodium channel modulator |

Non-limiting examples of suitable anthelminthics are named in the following, a few representatives have insecticidal and acaricidal activity in addition to the anthelminthic activity, and are partly already in the above list.

(A1) Praziquantel=2-cyclohexylcarbonyl-4-oxo-1,2,3,6,7,11b-hexahydro-o-4H-pyrazino[2,1-.alpha.]isoquinoline
(A2) Closantel=3,5-diiodo-N-[5-chloro-2-methyl-4-(a-cyano-4-chlorob-enzyl)phenyl]-salicylamide
(A3) Triclabendazole=5-chloro-6-(2,3-dichlorophenoxy)-2-methylthio-1H-benzimidazole
(A4) Levamisol=L-(+2,3,5,6-tetrahydro-6-phenylimidazo[2,1b]thiazo-le
(A5) Mebendazole=(5-benzoyl-1H-benzimidazol-2-yl)carbaminic acid methylester
(A6) Omphalotin=a macrocyclic fermentation product of the fungus *Omphalotus olearius* described In WO 97/20857
(A7) Abamectin=avermectin B1
(A8) Ivermectin=22,23-dihydroavermectin B1
(A9) Moxidectin=5-O-demethyl-28-deoxy-25-(1,3-dimethyl-1-butenyl)-6-,28-epoxy-23-(methoxyimino)-milbemycin B
(A10) Doramectin=25-cyclohexyl-5-O-demethyl-25-de(1-methylpropyl)-a-vermectin A1a
(A11) Milbemectin=mixture of milbemycin A3 and milbemycin A4
(A12) Milbemycinoxim=5-oxime of milbemectin
Non-Limitative Examples of Suitable Repellents and Detachers are:
(R1) DEET (N,N-diethyl-m-toluamide)
(R2) KBR 3023 N-butyl-2-oxycarbonyl-(2-hydroxy)-piperidine
(R3) Cymiazole=N,-2,3-dihydro-3-methyl-1,3-thiazol-2-ylidene-2,4-xy-lidene The aforementioned partners in the mixture are best known to specialists in this field. Most are described in various editions of the Pesticide Manual, The British Crop Protection Council, London, and others in the various editions of The Merck Index, Merck & Co., Inc., Rahway, N.J., USA or in patent literature. Therefore, the following listing is restricted to a few places where they may be found by way of example.

(I) 2-Methyl-2-(methylthio)propionaldehyde-O-methylcarbamoyloxime (Aldicarb), from The Pesticide Manual, 11.sup.th Ed. (1997), The British Crop Protection Council, London, page 26;
(II) S-(3,4-dihydro-4-oxobenzo[d]-[1,2,3]-triazin-3-ylmethyl)O,O-di-methyl-phosphorodithioate (Azinphos-methyl), from The Pesticide Manual, 11.sup.thEd. (1997), The British Crop Protection Council, London, page 67;
(III) Ethyl-N-[2,3-dihydro-2,2-dimethylbenzofuran-7-yloxycarbonyl-(-methyl)aminothio]-N-isopropyl-.beta.-alaninate (Benfuracarb), from The Pesticide Manual, 11.sup.thEd. (1997), The British Crop Protection Council, London, page 96;
(IV) 2-Methylbiphenyl-3-ylmethyl-(Z)-(1RS)-cis-3-(2-chloro-3,3,3-tr-ifluoroprop-1-enyl)-2,2-dimethylcyclopropanecarboxylate (Bifenthrin), from The Pesticide Manual, 11.sup.thEd. (1997), The British Crop Protection Council, London, page 118;
(V) 2-tert-butylimino-3-isopropyl-5-phenyl-1,3,5-thiadiazian-4-one (Buprofezin), from The Pesticide Manual, 11.sup.thEd. (1997), The British Crop Protection Council, London, page 157;
(VI) 2,3-Dihydro-2,2-dimethylbenzofuran-7-yl-methylcarbamate (Carbofuran), from The Pesticide Manual, 11.sup.thEd. (1997), The British Crop Protection Council, London, page 186;
(VII) 2,3-Dihydro-2,2-dimethylbenzofuran-7-yl-(dibutylaminothio)met-hylcarbamate (Carbosulfan), from The Pesticide Manual, 11.sup.thEd. (1997), The British Crop Protection Council, London, page 188;
(VIII) S,S'-(2-dimethylaminotrimethylene)-bis(thiocarbamate) (Cartap), from The Pesticide Manual, 11.sup.thEd. (1997), The British Crop Protection Council, London, page 193;
(IX) 1-[3,5-Dichloro-4-(3-chloro-5-trifluoromethyl-2-pyridyloxy)phe-nyl]-3-(2,6-difluorobenzoyl)-urea (Chlorfluazuron), from The Pesticide Manual, 11.sup.thEd. (1997), The British Crop Protection Council, London, page 213;
(X) O,O-diethyl-O-3,5,6-trichloro-2-pyridyl-phosphorothioate (Chlorpyrifos), from The Pesticide Manual, 11.sup.thEd. (1997), The British Crop Protection Council, London, page 235;
(XI) (RS)-.alpha.-cyano-4-fluoro-3-phenoxybenzyl-(1RS,3RS;1RS,3RS)-3-(2,2-dichlorovinyl)-2,2-di-methylcyclopropanecarboxylate (Cyfluthrin), from The Pesticide Manual, 11.sup.thEd. (1997), The British Crop Protection Council, London, page 293;
(XII) Mixture of (S)-.alpha.-cyano-3-phenoxybenzyl-(Z)-(1R,3R)-3-(2-1-chloro-3,3,3-trifluoropropenyl)-2,2-dimethylcyclopropanecarboxylate and (R)-.alpha.-cyano-3-phenoxybenzyl-(Z)-(1R,3)-3-(2-chloro-3,3,3-trifluoropropenyl)-2,2-dimethylcyclopropanecarboxylate (Lambda-Cyhalothrin), from The Pesticide Manual, 11.sup.thEd. (1997), The British Crop Protection Council, London, page 300;
(XIII) Racemate consisting of (S)-.alpha.-cyano-3-phenoxybenzyl-(2)-1-(1R,3R)-3-(2,2-dichlorovinyl)-2,2-dimethylcyclopropanecarboxylate and (R)-.alpha.-cyano-3-phenoxybenzyl-(1S,3S)-3-(2,2-dichlorovinyl)-2,2-dimethylcyclopropanecarboxylate (Alpha-cypermethrin), from The Pesticide Manual, 11.sup.thEd. (1997), The British Crop Protection Council, London, page 308;
(XIV) a mixture of the stereoisomers of (S)-.alpha.-cyano-3-phenoxy-benzyl (1RS,3RS,1 RS,3RS)-3-(2,2-dichlorovinyl)-2,2-dimethylcyclopropaneca-rboxylate (zeta-Cypermethrin), from The Pesticide Manual, 11.sup.thEd. (1997), The British Crop Protection Council, London, page 314;
(XV) (S)-.alpha.-cyano-3-phenoxybenzyl-(1R,3R)-3-(2,2-dibromovinyl)-1-2,2-dimethylcyclopropanecarboxylate (Deltamethrin), from The Pesticide Manual, 11.sup.thEd. (1997), The British Crop Protection Council, London, page 344;
(XVI) (4-chlorophenyl)-3-(2,6-difluorobenzoyl)urea (Diflubenzuron), from The Pesticide Manual, 11.sup.thEd. (1997), The British Crop Protection Council, London, page 395;
(XVII) (1,4,5,6,7,7-Hexachloro-8,9,10-trinorborn-5-en-2,3-ylenebism-ethylene)-sulphite (Endosulfan), from The Pesticide Manual, 11.sup.thEd. (1997), The British Crop Protection Council, London, page 459;
(XVIII) .alpha.-ethylthio-o-tolyl-methylcarbamate (Ethiofencarb), from The Pesticide Manual, 11.sup.thEd. (1997), The British Crop Protection Council, London, page 479;
(XIX) O,O-dimethyl-O-4-nitro-m-tolyl-phosphorothioate (Fenitrothion), from The Pesticide Manual, 11.sup.thEd. (1997), The British Crop Protection Council, London, page 514;
(XX) 2-sec-butylphenyl-methylcarbamate (Fenobucarb), from The Pesticide Manual, 11.sup.thEd. (1997), The British Crop Protection Council, London, page 516;
(XXI) (RS)-.alpha.-cyano-3-phenoxybenzyl-(RS)-2-(4-chlorophenyl)-3-methylbutyrate (Fenvalerate), from The Pesticide Manual, 11.sup.thEd. (1997), The British Crop Protection Council, London, page 539;

(XXII) S-[formyl(methyl)carbamoylmethyl]-O,O-dimethyl-phosphorodith-ioate (Formothion), from The Pesticide Manual, 11.sup.thEd. (1997), The British Crop Protection Council, London, page 625;
(XXIII) 4-Methylthio-3,5-xylyl-methylcarbamate (Methiocarb), from The Pesticide Manual, 11.sup.thEd. (1997), The British Crop Protection Council, London, page 813;
(XXIV) 7-Chlorobicyclo[3.2.0]hepta-2,6-dien-6-yl-dimethylphosphate (Heptenophos), from The Pesticide Manual, 11.sup.thEd. (1997), The British Crop Protection Council, London, page 670;
(XXV) 1-(6-chloro-3-pyridylmethyl)-N-nitroimidazolidin-2-ylidenamin-e (Imidacloprid), from The Pesticide Manual, 11.sup.thEd. (1997), The British Crop Protection Council, London, page 706;
(XXVI) 2-isopropylphenyl-methylcarbamate (Isoprocarb), from The Pesticide Manual, 11.sup.thEd. (1997), The British Crop Protection Council, London, page 729;
(XXVII) O,S-dimethyl-phosphoramidothioate (Methamidophos), from The Pesticide Manual, 11.sup.thEd. (1997), The British Crop Protection Council, London, page 808;
(XXVIII) S-Methyl-N-(methylcarbamoyloxy)thioacetimidate (Methomyl), from The Pesticide Manual, 11.sup.thEd. (1997), The British Crop Protection Council, London, page 815;
(XXIX) Methyl-3-(dimethoxyphosphinoyloxy)but-2-enoate (Mevinphos), from The Pesticide Manual, 11.sup.thEd. (1997), The British Crop Protection Council, London, page 844;
(XXX) O,O-diethyl-O-4-nitrophenyl-phosphorothioate (Parathion), from The Pesticide Manual, 11.sup.thEd. (1997), The British Crop Protection Council, London, page 926;
(XXXI) O,O-dimethyl-O-4-nitrophenyl-phosphorothioate (Parathion-methyl), from The Pesticide Manual, 11.sup.thEd. (1997), The British Crop Protection Council, London, page 928;
(XXXII) S-6-chloro-2,3-dihydro-2-oxo-1,3-benzoxazol-3-ylmethyl-O,O-diethyl-phosphordithioate (Phosalone), from The Pesticide Manual, 11.sup.thEd. (1997), The British Crop Protection Council, London, page 963;
(XXXIII) 2-Dimethylamino-5,6-dimethylpyrimidin-4-yl-dimethylcarbama- to (Pirimicarb), from The Pesticide Manual, 11.sup.thEd. (1997), The British Crop Protection Council, London, page 985;
(XXXIV) 2-isopropoxyphenyl-methylcarbamate (Propoxur), from The Pesticide Manual, 11.sup.thEd. (1997), The British Crop Protection Council, London, page 1036;
(XXXV) 1-(3,5-dichloro-2,4-difluorophenyl)-3-(2,6-difluorobenzoyl)u-rea (Teflubenzuron), from The Pesticide Manual, 11.sup.thEd. (1997), The British Crop Protection Council, London, page 1158;
(XXXVI) S-tert-butylthiomethyl-O,O-dimethyl-phosphorodithioate (Terbufos), from The Pesticide Manual, 11.sup.thEd. (1997), The British Crop Protection Council, London, page 1165;
(XXXVII) ethyl-(3-tert.-butyl-1-dimethylcarbamoyl-1H-1,2,4-triazol-5-yl-thio)-acetate, (Triazamate), from The Pesticide Manual, 11.sup.thEd. (1997), The British Crop Protection Council, London, page 1224;
(XXXVIII) Abamectin, from The Pesticide Manual, 11.sup.thEd. (1997), The British Crop Protection Council, London, page 3;
(XXXIX) 2-sec-butylphenyl-methylcarbamate (Fenobucarb), from The Pesticide Manual, 11.sup.thEd. (1997), The British Crop Protection Council, London, page 516; (XL) N-tert.-butyl-N'-(4-ethylbenzoyl)-3,5-dimethylbenzohydrazide (Tebufenozide), from The Pesticide Manual, 11.sup.thEd. (1997), The British Crop Protection Council, London, page 1147;
(XLI) (.+-.)-5-amino-1-(2,6-dichloro-.alpha.,.alpha.,.alpha.-triflu-oro-p-tolyl)-4-trifluoromethyl-sulphinylpyrazol-3-carbonitrile (Fipronil), from The Pesticide Manual, 11.sup.thEd. (1997), The British Crop Protection Council, London, page 545;
(XLII) (RS)-.alpha.-cyano-4-fluoro-3-phenoxybenzyl(1RS, 3RS;1 RS,3RS)-3-(2,2-dichlorovinyl)-2,2-dimethylcyclopropanecarboxylate (beta-Cyfluthrin), from The Pesticide Manual, 11.sup.thEd. (1997), The British Crop Protection Council, London, page 295;
(XLIII) (4-ethoxyphenyl)-[3-(4-fluoro-3-phenoxyphenyl)propyl](dimet-hyl)silane (Silafluofen), from The Pesticide Manual, 11.sup.thEd. (1997), The British Crop Protection Council, London, page 1105;
(XLIV) tert.-butyl (E)-.alpha.-(1,3-dimethyl-5-phenoxypyrazol-4-yl-methylenamino-oxy)-p-toluate (Fenpyroximate), from The Pesticide Manual, 11.sup.thEd. (1997), The British Crop Protection Council, London, page 530; (XLV) 2-tert.-butyl-5-(4-tert.-butylbenzylthio)-4-chloropyridazin-3-(2H)-one (Pyridaben), from The Pesticide Manual, 11.sup.thEd. (1997), The British Crop Protection Council, London, page 1161;
(XLVI) 4-[[4-(1,1-dimethylphenyl)phenyl]ethoxy]-quinazoline (Fenazaquin), from The Pesticide Manual, 11.sup.thEd. (1997), The British Crop Protection Council, London, page 507;
(XLVII) 4-phenoxyphenyl-(RS)-2-(pyridyloxy)propyl-ether (Pyriproxyfen), from The Pesticide Manual, 11.sup.thEd. (1997), The British Crop Protection Council, London, page 1073;
(XLVIII) 5-chloro-N-{2-[4-(2-ethoxyethyl)-2,3-dimethylphenoxy]ethyl-}-6-ethylpyrimidine-4-amine (Pyrimidifen), from The Pesticide Manual, 11.sup.thEd. (1997), The British Crop Protection Council, London, page 1070;
(XLIX) (E)-N-(6-chloro-3-pyridylmethyl)-N-ethyl-N'-methyl-2-nitrovi-nylidenediamine (Nitenpyram), from The Pesticide Manual, 11.sup.thEd. (1997), The British Crop Protection Council, London, page 880;
(L) (E)-N.sup.1-[(6-chloro-3-pyridyl)methyl]-N.sup.2-cyano-N.sup.1-methylacetamidine (NI-25, Acetamiprid), from The Pesticide Manual, 11.sup.thEd. (1997), The British Crop Protection Council, London, page 9;
(LI) Avermectin B.sub.1, from The Pesticide Manual, 11.sup.thEd. (1997), The British Crop Protection Council, London, page 3;
(LII) an insect-active extract from a plant, especially (2R,6aS, 12aS)-1,2,6,6a,12,12a-hexhydro-2-isopropenyl-8,9-dimethoxy-chrome-no[3,4-b]furo[2,3-h]chromen-6-one (Rotenone), from The Pesticide Manual, 11.sup.thEd. (1997), The British Crop Protection Council, London, page 1097; and an extract from *Azadirachta indica*, especially azadirachtin, from The Pesticide Manual, 11.sup.thEd. (1997), The British Crop Protection Council, London, page 59; and
(LII) a preparation which contains insect-active nematodes, preferably *Heterorhabditis bactedophora* and *Heterorhabditis megidis*, from The Pesticide Manual, 11.sup.thEd. (1997), The British Crop Protection Council, London, page 671; *Steinemema feltiae*, from The Pesticide Manual, 11.sup.thEd. (1997), The British Crop Protection Council, London, page 1115 and *Steinemema scaptedsci*, from The Pesticide Manual, 11.sup.thEd. (1997), The British Crop Protection Council, London, page 1116;
(LIV) a preparation obtainable from *Bacillus subtilis*, from The Pesticide Manual, 11.sup.thEd. (1997), The British Crop Protection Council, London, page 72; or from a strain of *Bacillus thuringiensis* with the exception of compounds isolated from GC91 or from NCTC11821; The Pesticide Manual, 11.sup.thEd. (1997), The British Crop Protection Council, London, page 73;

(LV) a preparation which contains insect-active fungi, preferably *Verticillium lecanii*, from The Pesticide Manual, 11.sup.th Ed. (1997), The British Crop Protection Council, London, page 1266; *Beauveda brogniartii*, from The Pesticide Manual, 11.sup.thEd. (1997), The British Crop Protection Council, London, page 85 and *Beauveda bassiana*, from The Pesticide Manual, 11.sup.thEd. (1997), The British Crop Protection Council, London, page 83;

(LVI) a preparation which contains insect-active viruses, preferably Neodipridon Sertifer NPV, from The Pesticide Manual, 11.sup.thEd. (1997), The British Crop Protection Council, London, page 1342; *Mamestra brassicae* NPV, from The Pesticide Manual, 11.sup.thEd. (1997), The British Crop Protection Council, London, page 759 and *Cydia pomonella* granulosis virus, from The Pesticide Manual, 11.sup.thEd. (1997), The British Crop Protection Council, London, page 291;

(CLXXXI) 7-chloro-2,3,4a,5-tetrahydro-2-[methoxycarbonyl(4-trifluor-omethoxyphenyl)-carbamoyl]indol[1,2e]oxazoline-4-a-carboxylate (DPX-MP062, Indoxycarb), from The Pesticide Manual, 11.sup.thEd. (1997), The British Crop Protection Council, London, page 453;

(CLXXXII) N'-tert.-butyl-N'-(3,5-dimethylbenzoyl)-3-methoxy-2-methyl-Ibenzohydrazide (RH-2485, Methoxyfenozide), from The Pesticide Manual, 11.sup.thEd. (1997), The British Crop Protection Council, London, page 1094; and (CLXXXIII) (N'-[4-methoxy-biphenyl-3-yl]-hydrazinecarboxylic acid isopropylester (D 2341), from Brighton Crop Protection Conference, 1996, 487-493; (R2) Book of Abstracts, 212th ACS National Meeting Orlando, Fla., Aug. 25-29 (1996), AGRO-020. Publisher: American Chemical Society, Washington, D.C. CONEN: 63BFAF.

As a rule, the anthelminthic compositions according to the invention contain 0.1 to 99% by weight, especially 0.1 to 95% by weight of active ingredient of Formula 1 mixtures thereof, 99.9 to 1% by weight, especially 99.8 to 5% by weight of a solid or liquid admixture, including 0 to 25% by weight, especially 0.1 to 25% by weight of a surfactant.

As noted above, in another embodiment of the process according to the invention, compounds of Formula 1 and the additional compounds noted hereinbefore may be applied in a distinct and separate manner over time.

The following TESTS demonstrate the control efficacy of compounds of this invention on specific pests. The pest control protection afforded by the compounds is not limited, however, to these species.

BIOLOGICAL EXAMPLES OF THE INVENTION

Test A

Adult *H. irritans exigua* Feeding Assay

A blood meal assay was used to determine the $LC_{50}$ for test compound (3-bromo-1-(3-chloro-2-pyridinyl)-N-[4-cyano-2-methyl-6-[(methylamino)carbonyl]phenyl]-1H-pyrazole-5-carboxamide) on adult *H. irritans exigua*. Six (6) serial dilutions of the test compound were prepared in decoagulated bovine blood that was stored refrigerated. Ivermectin was included as a positive control compound and a negative control was included in each assay. Flies were collected with a net immediately before each assay from yarded commercial cattle. About 100 adults were introduced into a mesh cage (30×30×30 cm) containing one cotton gauze (4×4×1 cm) soaked in one blood/insecticide concentration. There were 3 replicate cages of each blood/insecticide concentration. Blood gauzes were replaced every 12 hours. The untreated control cages received untreated decoagulated blood. All cages were labelled and stored for 72 hours at 25-27° C. in the dark at ambient relative humidity (70-85%). Every 12 hours the numbers of dead flies were counted in each cage. At 72-96 hours all flies were counted and percentage mortality was calculated. Data was subjected to log-probit analysis to determine the $LC_{50}$ if there is a dose response in the assay.

| Adult *H. irritans exigua* feeding assay | | | | |
|---|---|---|---|---|
| | | % Adult mortality Exposure time | | |
| Compound | Concentration | 7 hr | 17 hr | 24 hr |
| Test compound | 600 ppb | 80.5 | 94.7 | 96.5 |
| | 400 ppb | 78.8 | 89.8 | 94.9 |
| | 200 ppb | 77.3 | 78.8 | 80.3 |
| Ivermectin | 600 ppb | 86.0 | 95.5 | 100.0 |
| | 400 ppb | 80.1 | 94.2 | 98.0 |
| | 200 ppb | 78.5 | 91.8 | 93.1 |
| Control Mortality | | 10.8 | 16.8 | 21.0 |

Test B

Adult *A. aegypti* Contact Assay

Adult *A. aegypti* were exposed to six rates of the positive control compound permethrin and the experimental compounds diluted with acetone. The dilutions of test compound (3-bromo-1-(3-chloro-2-pyridinyl)-N-[4-cyano-2-methyl-6-[(methylamino)carbonyl]phenyl]-1H-pyrazole-5-carboxamide)used were 0 ppm (acetone only), 0.1 ppm, 1 ppm, 10 ppm, 20 ppm, 50 ppm, 100 ppm, 500 ppm and 1000 ppm. Each rate was replicated 5 times. The test was conducted in 100 mL conical flasks. The entire inside of the flasks was coated with Coatasil the day before the treatments are applied. A 0.5 ml aliquot of each rate was applied to the bases only of the flasks. At 24 hours after the surfaces had been treated adult *A. aegypti* were anaesthetised using food grade carbon dioxide and 10 mosquitoes were introduced to each conical flask and the mouths of the flasks covered with parafilm. Small holes were made in the parafilm to allow gas exchange. The bioassay was run for 8 hrs at 25±2° C. and relative humidity of approximately 70%.

| Mosquito adults *A. aegypti* contact assay | | |
|---|---|---|
| Compound | LC50 (ug/flask) | LC90 (ug/flask) |
| Test compound | 0.025 | 0.033 |
| Permethrin | 0.025 | 0.046 |

Untreated control mortality - 6%

Test C

In Vivo Evaluation Against Artificial Infestations with Cat Fleas (*C. felis*) and Brown Dog Ticks (*R. sanguineus*) on Dogs Twenty five dogs were used in this study that investigated the efficacy of test compound (3-bromo-1-(3-chloro-2-pyridinyl)-N-[4-cyano-2-methyl-6-[(methylamino)carbonyl]phenyl]-1H-pyrazole-5-carboxamide) against fleas and ticks. Two groups (one treated and one untreated) of five dogs were used to evaluate the flea efficacy whilst two groups of five dogs (one treated and one untreated) were used to investigate the tick efficacy. The dogs in the respective groups were infested weekly with 40 unfed adult ticks and 100 cat fleas. One group was treated with ADVANTIX and served as a positive control. The dogs in this group were infested simultaneously with fleas and ticks. Test compound was formulated in NMP. The treatment was applied topically via syringe on the dorsal line of the animals as a line-on at 60 mg/kg dose rate. The efficacy of the compound was assessed by weekly tick and flea counts. The weekly counts generated in the treated groups were compared to the positive and negative untreated control (UTC) group counts to evaluate efficacy of Test compound.

In Vivo Evaluation Against Artificial Infestations with *C. felis* and *R. sanguineus* on Dogs

| Group | Treatment | Day 2 | Day 9 | Day 16 | Day 23 | Day 29 |
|---|---|---|---|---|---|---|
| Flea efficacy (%) compared to the untreated control | | | | | | |
| 4 | Test compound | 99.6 | 99.7 | 99.7 | 98.7 | 97.3 |
| 5 | ADVANTIX | 100 | 100 | 89.0 | 76.7 | 69.1 |
| UTC (Mean # of fleas) | Vehicle (NMP) | 57.0 | 73.8 | 78.2 | 76.4 | 73.2 |
| Tick efficacy (%) compared to the untreated control | | | | | | |
| 3 | Test compound | 74.0 | 94.9 | 95.0 | 90.6 | 86.2 |
| 5 | ADVANTIX | 44.0 | 99.3 | 89.7 | 84.2 | 79.7 |
| UTC (Mean # of ticks) | Vehicle (NMP) | 10.0 | 27.6 | 25.2 | 27.8 | 24.6 |

Small numbers of engorged ticks were found on dogs in both the experimental and positive control treatment groups at all assessment times. Test compound provided a similar level of protection against ticks to that of the positive control product ADVANTIX, with slightly lower numbers of live ticks collected from the dogs during all but one assessment over the 30 day period. At 48 hours after treatment, the test compound achieved 74% efficacy compared to the negative control. This result was 30% higher than the ADVANTIX that gave 44% efficacy. Test compound provided over 94.9%, 90.5% and 90.6% efficacy at 9, 16 and 23 days post-treatment which was a level of control similar to the ADVANTIX with 99.3%, 89.7% and 84.2% respectively. The test compound continued to provide a high level of protection at 30 days post treatment, with 86.2% efficacy compared to 79.7% provided by the ADVANTIX.

Overall, the test compound treatment was more effective against fleas than the positive control product, with over 99.5% efficacy during the first three assessments at 2, 9 and 16 days post-treatment and 97.3% efficacy at 30 days post-treatment. Although the ADVANTIX achieved 100% efficacy during the first 9 days after application, this dropped to below 90% by day 16 and below 70% by day 30.

Test D

In Vivo Evaluation Against Artificial Infestations with Cat Fleas (*C. felis*) on Mice For evaluating control of the cat flea (*Ctenocephalides felis* Bouche), a CD-1® mouse (about 30 g, male, obtained from Charles River Laboratories, Wilmington, Mass.) was orally dosed with test compound in an amount of 10 mg/kg solubilized in propylene glycol/glycerol formal (60:40). Two hours after oral administration of the test compound, approximately 8 to 16 adult fleas were applied to each mouse. The fleas were then evaluated for mortality 48 hours after flea application to the mouse.

3-bromo-1-(3-chloro-2-pyridinyl)-N-[4-cyano-2-methyl-6-[(methylamino)carbonyl]phenyl]-1H-pyrazole-5-carboxamide caused 45% mortality.

Although the present invention and its advantages have been described in detail, it should be understood that various changes, substitutions and alterations can be made herein without departing from the spirit and scope of the invention as defined by the appended claims.

What is claimed is:

1. A method of controlling infestation of an ectoparasite selected from the group consisting of fleas and ticks on a homeothermic animal which is either a dog or cat by topical spot on administration to the animal, a composition comprising a parasiticidally effective amount of the compound

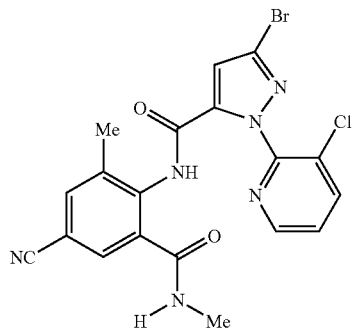

or an N-oxide or a pharmaceutically or veterinarily acceptable salt thereof; wherein the parasiticidally effective amount of the compound is between 0.1 mg/kg to 200 mg/kg of animal body weight and wherein the control of fleas and ticks persists for at least thirty days.

2. The method of claim 1 wherein the animal is a cat.

3. The method of claim 1 wherein the animal is a dog.

4. The method of any of claims 1, 2 or 3 wherein the composition comprises an additional component selected from the group consisting of solvents and/or carriers, emulsifiers and/or dispersing agents.

5. The method of claim 1 wherein the compound is neither an N-oxide or a salt.

* * * * *